(12) United States Patent
O'Mahony et al.

(10) Patent No.: US 11,623,020 B2
(45) Date of Patent: Apr. 11, 2023

(54) HYDROPHILIC COATINGS AND METHODS OF FORMING THE SAME

(71) Applicant: Hollister Incorporated, Libertyville, IL (US)

(72) Inventors: John P. O'Mahony, Ardnacrusha (IE); David J. Farrell, Ballina (IE)

(73) Assignee: Hollister Incorporated, Libertyville, IL (US)

( * ) Notice: Subject to any disclaimer, the term of this patent is extended or adjusted under 35 U.S.C. 154(b) by 154 days.

(21) Appl. No.: 16/830,069

(22) Filed: Mar. 25, 2020

(65) Prior Publication Data

US 2020/0222587 A1   Jul. 16, 2020

Related U.S. Application Data

(62) Division of application No. 15/564,354, filed as application No. PCT/US2016/027534 on Apr. 14, 2016, now Pat. No. 10,617,789.

(60) Provisional application No. 62/148,473, filed on Apr. 16, 2015.

(51) Int. Cl.
| | |
|---|---|
| *A61L 27/34* | (2006.01) |
| *A61L 29/08* | (2006.01) |
| *C08L 39/06* | (2006.01) |
| *C08L 71/02* | (2006.01) |

(52) U.S. Cl.
CPC ............. *A61L 27/34* (2013.01); *A61L 29/085* (2013.01); *C08L 39/06* (2013.01); *C08L 71/02* (2013.01); *A61L 2420/06* (2013.01); *A61L 2420/08* (2013.01); *C08L 2203/02* (2013.01)

(58) Field of Classification Search
CPC .... B05D 3/06; B05D 5/00; A61K 9/00; A61L 29/14; A61L 27/34; A61L 29/085; A61F 13/00
See application file for complete search history.

(56) References Cited

U.S. PATENT DOCUMENTS

| | | |
|---|---|---|
| 4,906,237 A | 3/1990 | Johansson et al. |
| 5,405,366 A | 4/1995 | Fox et al. |
| 5,480,717 A | 1/1996 | Kundel |
| 5,576,072 A | 9/1996 | Hostettler et al. |
| 5,693,034 A | 12/1997 | Buscemi et al. |
| 5,702,754 A | 12/1997 | Zhong |
| 5,789,018 A | 8/1998 | Engelson et al. |

(Continued)

FOREIGN PATENT DOCUMENTS

| | | |
|---|---|---|
| CN | 101455861 A | 6/2009 |
| CN | 101612421 A | 12/2009 |

(Continued)

OTHER PUBLICATIONS

Office Action, Chinese App. No. 201680021597.5, dated May 18, 2020.

(Continued)

*Primary Examiner* — Dah-Wei D. Yuan
*Assistant Examiner* — Andrew J Bowman
(74) *Attorney, Agent, or Firm* — Cook Alex Ltd.

(57) ABSTRACT

Hydrophilic coatings including a base coat layer and a top coat layer wherein at least one of the base coat and top coat compositions that form the hydrophilic coatings comprises a diacrylate compound have a number average molecular weight less than 1000.

34 Claims, 9 Drawing Sheets

(56) References Cited

U.S. PATENT DOCUMENTS

| | | | |
|---|---|---|---|
| 5,800,412 A | 9/1998 | Zhang et al. | |
| 5,919,570 A | 7/1999 | Hostettler et al. | |
| 5,962,620 A | 10/1999 | Reich et al. | |
| 5,993,972 A | 11/1999 | Reich et al. | |
| 5,997,517 A | 12/1999 | Whitbourne | |
| 6,048,620 A | 4/2000 | Zhong | |
| 6,110,483 A | 8/2000 | Whitbourne et al. | |
| 6,120,904 A | 9/2000 | Hostettler et al. | |
| 6,221,425 B1 | 4/2001 | Michal et al. | |
| 6,306,176 B1 | 10/2001 | Whitbourne | |
| 6,340,465 B1 | 1/2002 | Hsu et al. | |
| 6,358,557 B1 | 3/2002 | Wang et al. | |
| 6,387,080 B1 | 5/2002 | Rodsten | |
| 6,656,517 B2 | 12/2003 | Michal | |
| 6,866,936 B2 | 3/2005 | Opolski | |
| 6,986,868 B2 | 1/2006 | Madsen | |
| 7,008,979 B2 | 3/2006 | Schottman et al. | |
| 7,264,859 B2 | 9/2007 | Rouns | |
| 7,534,495 B2 | 5/2009 | Eramo | |
| 7,544,381 B2 | 6/2009 | Kangas | |
| 7,691,476 B2 | 4/2010 | Finley | |
| 7,820,284 B2 | 10/2010 | Terry | |
| 7,820,734 B2 | 10/2010 | McGhee | |
| 7,833,475 B2 | 11/2010 | Madsen | |
| 8,110,242 B2 | 2/2012 | Hawkins et al. | |
| 8,133,580 B2 | 3/2012 | Dias et al. | |
| 8,163,327 B2 | 4/2012 | Finley | |
| 8,287,890 B2 | 10/2012 | Elton | |
| 8,377,498 B2 | 2/2013 | Rindlav-Westling et al. | |
| 8,378,011 B2 | 2/2013 | Eramo, Jr. et al. | |
| 8,512,795 B2 | 8/2013 | Dias et al. | |
| 8,513,320 B2 | 8/2013 | Rooijmans | |
| 8,541,498 B2 | 9/2013 | Sandhu et al. | |
| 8,728,508 B2 | 5/2014 | Nielsen et al. | |
| 8,747,940 B2 | 6/2014 | Lee et al. | |
| 8,808,238 B2 | 8/2014 | Tsubooka et al. | |
| 8,809,411 B2 | 8/2014 | Rooijmans | |
| 8,828,546 B2 | 9/2014 | Dias et al. | |
| 8,871,869 B2 | 10/2014 | Dias et al. | |
| 8,888,759 B2 | 11/2014 | Schmid et al. | |
| 8,932,662 B2 | 1/2015 | Nielsen et al. | |
| 8,957,125 B2 | 2/2015 | Belt et al. | |
| 9,050,180 B1 | 6/2015 | Kong et al. | |
| 9,428,668 B2 | 8/2016 | Lustgarten | |
| 9,610,426 B2 | 4/2017 | Tsubooka et al. | |
| 9,737,639 B2 | 8/2017 | Babcock | |
| 9,782,521 B2 | 10/2017 | Omata et al. | |
| 9,839,725 B2 | 12/2017 | Delaney, Jr. et al. | |
| 10,098,988 B2 | 10/2018 | Kohama et al. | |
| 10,124,088 B2 | 11/2018 | Chappa et al. | |
| 10,213,529 B2 | 2/2019 | Slager | |
| 10,238,832 B2 | 3/2019 | Gustavsson et al. | |
| 2003/0060783 A1 | 3/2003 | Koole et al. | |
| 2003/0232895 A1* | 12/2003 | Omidian | C08F 220/06 521/99 |
| 2004/0039437 A1 | 2/2004 | Sparer et al. | |
| 2004/0086722 A1 | 5/2004 | Madsen | |
| 2005/0054774 A1 | 3/2005 | Kangas | |
| 2005/0137582 A1 | 6/2005 | Kull-Osterlin et al. | |
| 2005/0147735 A1 | 7/2005 | Lowery et al. | |
| 2005/0202060 A1 | 9/2005 | Wu et al. | |
| 2005/0214443 A1 | 9/2005 | Madsen | |
| 2008/0003348 A1 | 1/2008 | Madsen | |
| 2008/0033373 A1 | 2/2008 | Koole et al. | |
| 2008/0125513 A1 | 5/2008 | Kristiansen | |
| 2008/0193497 A1 | 8/2008 | Samuelsen et al. | |
| 2008/0292776 A1* | 11/2008 | Dias | C08J 7/043 427/2.24 |
| 2008/0306455 A1 | 12/2008 | Dias et al. | |
| 2009/0041923 A1 | 2/2009 | Lin et al. | |
| 2009/0169715 A1 | 7/2009 | Dias et al. | |
| 2009/0188857 A1 | 7/2009 | Moore et al. | |
| 2009/0232871 A1 | 9/2009 | Hitz et al. | |
| 2010/0076546 A1 | 3/2010 | Dias et al. | |
| 2010/0086580 A1 | 4/2010 | Nyman et al. | |
| 2010/0114042 A1 | 5/2010 | Dias et al. | |
| 2010/0119833 A1 | 5/2010 | Madsen et al. | |
| 2011/0059874 A1 | 3/2011 | Rooijmans et al. | |
| 2011/0305898 A1* | 12/2011 | Zhang | B32B 27/28 428/336 |
| 2013/0006175 A1 | 1/2013 | Elton | |
| 2013/0109262 A1 | 5/2013 | Zhou | |
| 2013/0115466 A1 | 5/2013 | Madsen et al. | |
| 2013/0123664 A1 | 5/2013 | Lin et al. | |
| 2013/0136847 A1 | 5/2013 | Lee et al. | |
| 2013/0158518 A1 | 6/2013 | Li et al. | |
| 2014/0180221 A1 | 6/2014 | Dias et al. | |
| 2014/0190846 A1 | 7/2014 | Belt | |
| 2014/0294958 A1 | 10/2014 | Belt et al. | |
| 2014/0363562 A1 | 12/2014 | Nielsen et al. | |
| 2015/0018431 A1 | 1/2015 | Zeng et al. | |
| 2015/0038947 A1 | 2/2015 | Schmid et al. | |
| 2015/0051556 A1 | 2/2015 | Young | |
| 2016/0058913 A1 | 3/2016 | Dimitrievska et al. | |
| 2016/0175489 A1 | 6/2016 | Babcock et al. | |
| 2016/0310643 A1 | 10/2016 | Dias et al. | |
| 2016/0325024 A1 | 11/2016 | Lin | |
| 2017/0157298 A1* | 6/2017 | Diemeer | A61L 29/06 |
| 2019/0030214 A1 | 1/2019 | Montes de Oca et al. | |

FOREIGN PATENT DOCUMENTS

| | | |
|---|---|---|
| CN | 102325553 A | 1/2012 |
| CN | 102973987 A | 3/2013 |
| CN | 102973987 A | 3/2013 |
| CN | 104042295 A | 9/2014 |
| CN | 105153924 | 10/2017 |
| EP | 0612253 A3 | 5/1993 |
| EP | 0639990 B1 | 3/1995 |
| EP | 0604103 B1 | 3/1999 |
| EP | 1003571 B1 | 6/2005 |
| EP | 1696977 A2 | 7/2005 |
| EP | 0971753 B1 | 10/2005 |
| EP | 2090628 A1 | 8/2009 |
| EP | 1841807 B1 | 4/2010 |
| EP | 2177238 A1 | 4/2010 |
| EP | 2191888 A1 | 6/2010 |
| EP | 1534356 A1 | 7/2010 |
| EP | 1827718 B1 | 6/2011 |
| EP | 2776015 | 5/2013 |
| EP | 2252661 B1 | 10/2016 |
| EP | 2700420 B1 | 10/2016 |
| EP | 1578850 B1 | 2/2017 |
| PL | 216307 | 3/2014 |
| WO | WO 9416747 A1 | 8/1994 |
| WO | WO 9529722 A1 | 11/1995 |
| WO | WO 9623602 A1 | 8/1996 |
| WO | WO 9858990 A1 | 12/1998 |
| WO | WO 2006/037321 A1 | 4/2006 |
| WO | WO 2006037321 A1 | 4/2006 |
| WO | WO 2011/152967 A2 | 12/2011 |
| WO | WO 2011152967 A2 | 12/2011 |
| WO | WO2014/092660 | 6/2014 |
| WO | WO 2014/092660 | 6/2014 |
| WO | 2016001331 A1 | 7/2015 |
| WO | WO 2016/001331 A1 | 1/2016 |
| WO | WO-2016001331 A1 | 1/2016 |

OTHER PUBLICATIONS

Chinese Appl. No. 201680021597.5—Office Action from Chinese Patent Office dated Apr. 20, 2021.

Butruk Beata et al. "Polyvinylpyrrolidone-based coatings or polyurethanes—The effect of reagent concentration on their chosen physical properties", Chemical And Process Engineering, 2012, vol. 33 no. 4, pp. 563-571, DOI: 10.2478/v10176-012-0046-6.

Notification of Transmittal of The International Search Report, International Search Report and Written Opinion for PCT/US2016/027534 dated Oct. 26, 2017.

European Appl. No. 16719632.8—Official Communication from European Patent Office dated Aug. 1, 2019.

Australian Appl. No. 2016248234—Examination Report No. 1 from Australian Patent Office dated Sep. 11, 2019.

(56) References Cited

OTHER PUBLICATIONS

Butruk Beata et al. "Polyvinylpyrrolidone-based coatings or polyurethanes—The effect of reagent concentration on their chosen physical properties", Chemical And Process Engineering, 2012, vol. 33 no. 4, pp. 563-571, DOI: 10.2478/10176-012-0046-6.
Notification of Transmittai of the International Search Report and The Written Opinion of the ISA for PCT/US2016/027534 dated Sep. 2, 2017 (Sep. 2, 2017).
Australian Appl. No. 2016248234—Examination Report No. 1 from Austalian Patent Office dated Sep. 11, 2019.
Chinese Appl. No. 201680021597.5—Office Action from Chinese Patent Office dated May 18, 2020.
Chinese Appl. No. 201680021597.5—Office Action from Chinese Patent Office dated Nov. 12, 2020.
Extended European Search Report Issued in European Application No. 21170364.0, dated Aug. 13, 2021.
Notice of Opposition against European Patent No. 3283136, dated Mar. 2, 2022.
Wyman, "Hydrophilic coatings for biomedical applications in and ex vivo", in coatings for Biomedical Applications, DSM Biomedical Materials, the Netherlands, pp. 3-42, (2012).
Bercea, "Poly(vinylpyrrolidone)—A Versatile Polymer for Biomedical and Beyond Medical Applications", Polymer-Plastics Technology and Engineering, vol. 54, pp. 923-943 (2015).

\* cited by examiner

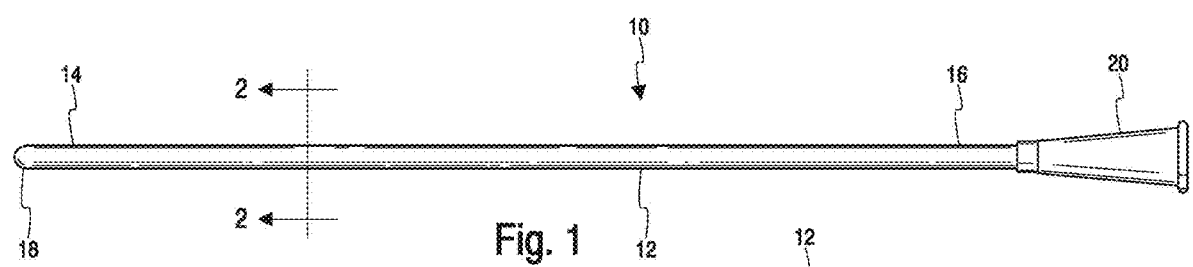
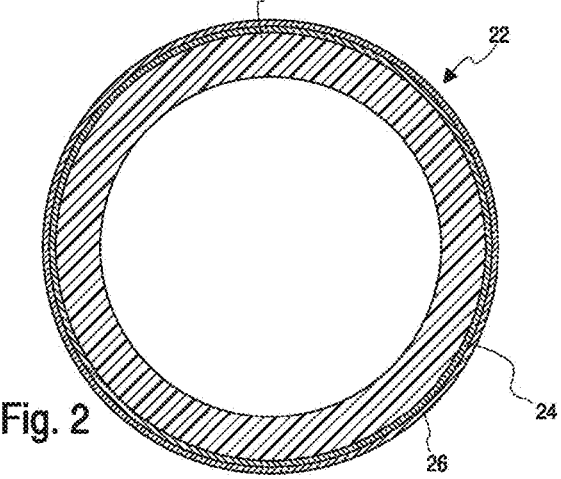

HYDROPHILIC COATINGS AND METHODS OF FORMING THE SAME

RELATED APPLICATION

The present application is a divisional application of U.S. patent application Ser. No. 15/564,354, filed Oct. 4, 2017, now U.S. Pat. No. 10,617,789, which is the U.S. National Stage of P.C.T. International Patent Application No. PCT/US2016/027534, filed Apr. 14, 2016, which claims the benefit and priority of U.S. Provisional Patent Application No. 62/148,473, filed Apr. 16, 2015, all of which are hereby incorporated herein by reference.

TECHNICAL FIELD

The present disclosure generally relates to hydrophilic coatings that include a hydrophilic polymer and a low molecular weight diacrylate. More particularly, the present disclosure relates to hydrophilic coatings that include a base coat layer and a top coat layer and to methods for forming such hydrophilic coatings. Furthermore, the present disclosure relates to medical devices, and in particular tubular medical devices, having hydrophilic coatings applied thereto and a method for providing such medical devices.

BACKGROUND

It is desirable for medical devices that are inserted into the body to have a lubricated or lubricious outer surface to facilitate insertion into and/or removal from the body. Such devices may include, for example, urinary catheters, endoscopes, cardiovascular catheters, syringes, vascular stents, etc. Such medical devices may have a lubricant gel placed on the outer surface of the device or may have a hydrophilic coating or layer disposed on the outer surface of the device. Hydrophilic coatings are becoming the preferred method of providing a lubricious surface because of their high lubricity and ease of use. Hydrophilic coatings become slippery or lubricous when wetted with a wetting fluid, such as saline or water. The wetted lubricous hydrophilic coating eases insertion and removal of the device, minimizes soft tissue damage and reduces overall discomfort during use of the medical device.

When a medical device having a hydrophilic coating is used, the hydrophilic coating is typically wetted for a certain period of time prior to use to activate the hydrophilic coating. For example, the user may immerse or otherwise contact the hydrophilic coating with a wetting fluid to wet or activate the coating. In some instances, the medical device is packaged in a packaging that includes liquid or vapor water within the package that hydrates the coating while the device is in the package so that the device is ready to use right out of the package.

Hydrophilic coatings are oftentimes applied to the surfaces of medical devices by a dip coating process that includes dipping the medical device into a base coat composition which typically includes a solvent, one or more polymers and additives and/or agents. The base coat composition is then cured to form a base coat layer. The medical device is then dipped into a top coat composition to apply the top coat composition over the base coat layer. The top coat composition oftentimes includes a solvent, one or more hydrophilic polymers, and other polymers, additives and/or agents. The top coat composition is then cured to form the hydrophilic coating, which becomes lubricious when wetted.

It is well-known that there are challenges in sterilizing and storing hydrophilic coatings in a "wet" state. For example, it is known that most hydrophilic coatings lose their water retention, have reduced attachment to the medical device and/or that the coefficient of friction increases when the coating is stored in water for an extended period of time and/or after being irradiation sterilized.

SUMMARY

The present disclosure provides formulations of base coat and top coat compositions that are particularly useful for forming hydrophilic coatings on surfaces of medical devices and in particular, urinary catheters. The present disclosure also discloses hydrophilic coatings that are formed from such top coat composition and/or base coat compositions.

In one aspect of the present disclosure, the base coat composition and the top coat composition that form the hydrophilic coating of the present disclosure include polyethylene glycol diacrylate (PEGDA) and a hydrophilic polymer. The PEGDA may have a number average molecular weight of less than 1000 or less than 900 or between about 200 and about 1000 and preferably between 400 and 900 and more preferably between 400 and 600. The base coat composition may also include other components, such as a curing agent and solvent. The top coat composition may also, optionally, include other components such as a curing agent, antioxidant, plasticizer, solvent and/or polyelectrolyte.

In one aspect, a medical device including a hydrophilic coating disposed on a surface of the medical device includes a base coat layer disposed on the surface of the medical device and a top coat layer disposed on the base coat layer wherein the top coat layer is formed from a blend comprising a hydrophilic polymer and polyethylene glycol diacrylate having a number average molecular weight of less than about 1000.

In another aspect, a hydrophilic coating includes an outer layer formed from a hydrophilic polymer and polyethylene glycol diacrylate having a number average molecular weight of less than about 1000.

In yet another aspect, a method of forming a hydrophilic coating on a surface of a medical device wherein the method includes applying a base coat composition to the surface of the medical device and curing the base coat composition to form a base coat layer. A top coat composition is applied to the base coat layer. The top coat composition includes a hydrophilic polymer and polyethylene diacrylate having a number average molecular weight of less than 1000. The top coat composition is then cured to form a top coat layer.

In yet another aspect, a medical device including a hydrophilic coating disposed on a surface of the medical device includes a base coat layer disposed on the surface of the medical device wherein the base coat layer is formed from a blend comprising a hydrophilic polymer and polyethylene glycol diacrylate having a number average molecular weight of less than about 1000. The device further includes a top coat layer disposed on the base coat layer.

In a further aspect, a medical device including a hydrophilic coating disposed on a surface of the medical device includes a base coat layer disposed on the surface of the medical device wherein the base coat layer is formed from a blend comprising a cellulose based polymer and a hydrophilic polymer. The device also includes a top coat layer disposed on the base coat layer wherein the top coat layer includes a hydrophilic polymer.

BRIEF DESCRIPTION OF DRAWINGS

FIG. 1 is a top plan view of a catheter of the present disclosure;

FIG. 2 is a cross-sectional view of the catheter of FIG. 1, taken along line 2-2;

DETAILED DESCRIPTION

Figure 3:
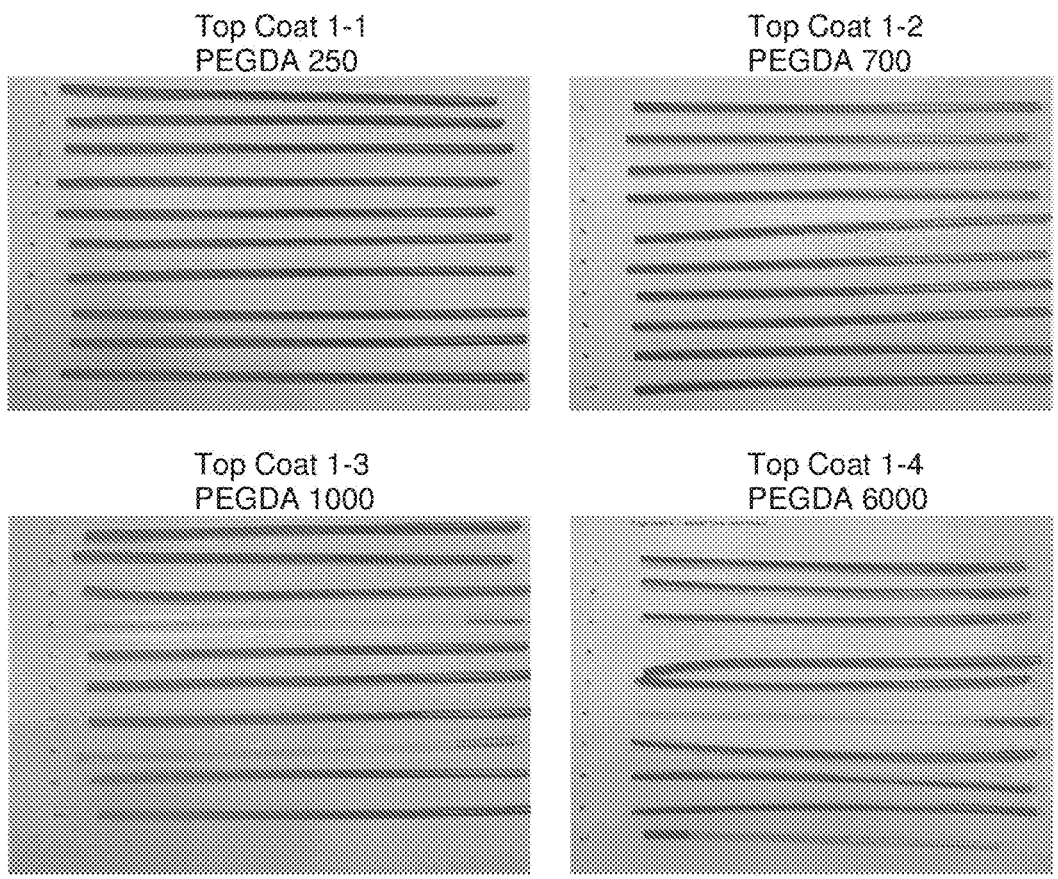
FIG. 3 are photographs of catheter tubes showing the visual results of the dye tests of Example 1.

The present disclosure discloses hydrophilic coatings that become lubricious when wetted with water or other suitable wetting agents wherein the coatings include a low molecular weight diacrylate compound, such as a diacrylate oligomer, and a hydrophilic polymer. In one embodiment the diacrylate compound is polyethylene glycol diacrylate (PEGDA). The present disclosure also discloses base coat and top coat compositions that may be used to form such hydrophilic coatings. The base coat and top coat compositions may be solutions or dispersions that are applied to the surface of a substrate, and then cured and/or dried to form the base coat and top coat layers of the hydrophilic coating. While the base coat and top coat compositions disclosed herein and coatings formed therefrom are described relative to urinary catheters, the compositions and coatings may be used to coat virtually any medical device for which it is desired to provide a lubricous hydrophilic coating on the surface thereof. The coatings and compositions are particularly useful for medical devices that are intended to be inserted into and removed from the body, such as urinary catheters, endoscopes, drainage catheters, etc.

The base coat compositions and top coat compositions disclosed herein may be used with one another to form lubricious hydrophilic coatings on a substrate. While the base coat and top coat compositions may be used with each other to form hydrophilic coatings, such base coat and top coat compositions are not required to be used with each other. That is, the base coat composition disclosed herein may not only be used with the top coat compositions disclosed herein but may also be used with other top coat compositions to form a hydrophilic coating on a medical device. Similarly, the top coat compositions disclosed herein may not only be used with the base coat compositions disclosed herein but may also be used with other base coat compositions to form a hydrophilic coating on the surface of a medical device. Furthermore, the top coat compositions may be applied directly to the surface of the substrate to form a hydrophilic coating on the substrate.

Referring to FIG. 1, there is shown a urinary catheter 10 having a catheter tube 12 including a proximal insertion end portion 14 and a distal drainage end portion 16. The proximal insertion end portion 14 includes an insertion tip 18 and the drainage end portion 16 optionally includes a drainage member, such as funnel 20. The insertion tip 18 also includes eyelets or drainage openings (not shown) for the passage of urine into the tube 12 when the insertion tip is inserted into the bladder. Turning to FIG. 2, the catheter tube 12 includes a hydrophilic coating 22 disposed thereon from the insertion tip 18 to a location at or adjacent to the distal end portion 16. In the illustrated embodiment, hydrophilic coating 22 includes a base coat or inner layer 24 disposed on the surface of catheter tube 12 and a top coat or outer layer 26 disposed on the base coat layer 24. In this embodiment, the base coat layer 24 which covers the catheter tube 12 and serves as a tie or adhesive layer that adheres to both the surface of the catheter and the top coat layer 26. In an alternative embodiment the top coat or outer layer 26 may be applied directly to the substrate without the use of a base coat layer.

The base coat or inner layer 24 may be formed from a blend including a film forming polymer, such as a hydrophilic polymer, and a diacrylate compound having a number average molecular weight (Mn) of less than about 1000 or less than about 900, preferably less than about 600, more preferably between about 200 and about 600, and even more preferably between about 400 and about 600. For example, the base coat layer may be formed from a base coat composition that includes a hydrophilic polymer, and PEGDA oligomer dissolved or dispersed in a solvent. The PEGDA may have a Mn of less than about 1000 or less than about 900. In one embodiment, the PEGDA has Mn of less than about 600. In another embodiment, the PEGDA has Mn of between about 200 and about 600. In yet another embodiment, the PEGDA has a Mn of between about 400 and about 600.

The film forming polymer may be, for example, a hydrophilic polymer, such as polyvinylpyrrolidone (PVP), polyethylene oxide, methyl cellulose, ethyl cellulose, polyethylene glycol, hydroxyl methylcellulose, hydroxypropyl cellulose, hydroxypropyl methylcellulose, carboxymethyl cellulose, polyvinyl alcohol, or mixtures thereof. In one embodiment, the film forming polymer is a polymer having a Mw above 500,000. For example, the film forming polymer may be PVP having a Mw of at least 500,000. In one embodiment of the base coat composition, the PVP may have a Mw of 1.3 m as determined by light scattering.

The base coat composition may also include a curing agent, such as a photoinitiator, which may be for example a type I photoinitiator, such as Irgacure 2959. The base coat composition also includes a solvent, such as water, ethanol, methanol, isopropyl alcohol, propanol or mixtures thereof. The base coat composition may optionally include additives such as antioxidants or antimicrobials.

In one embodiment, the solid components of the base coat composition in the dry state (without solvent) may include PEGDA in an amount of between about 5 wt % and about 90 wt % of the total solids and a film forming polymer(s) in an amount of between about 10 wt % and about 95 wt % of the total solids. The base coat composition in the dry state may also include a curing agent in the amount of between about 0.1 wt % and about 5 wt % of the total solids. In other embodiments, the solid components in the dry state may include PEGDA in an amount between about 15 wt % and about 25 wt % of the total solids and a film forming polymer(s) in an amount between about 75 wt % and about 85 wt %.

When the solid components are mixed with a solvent to form the base coat composition, the composition may include PEGDA in an amount between about 0.1 wt % and about 5 wt % of the total composition, an amount of film forming polymer(s) of between about 0.5 wt % and about 10 wt %, an amount of solvent of between about 90 wt % and about 99 wt %, and an amount of curing agent of between about 0.01 wt % and about 1 wt %.

In one embodiment, the base coat composition may include:

| | |
|---|---|
| PEGDA | 4.25 g |
| PVP K90 | 0.75 g |
| Irgacure 2959 | 0.2 g |
| Ethanol | 94.8 ml |

In another embodiment, the base coat composition may include:

| | |
|---|---|
| PEGDA | 4.25 g |
| Ethyl Cellulose 10cP | 0.75 g |
| Irgacure 2959 | 0.2 g |
| Ethanol | 94.8 ml |

In yet another embodiment, the base coat composition may include

| | |
|---|---|
| PEGDA | 4.25 g |
| PVP K90 | 0.50 g |
| Ethyl Cellulose 10cP | 0.25 g |
| Irgacure 2959 | 0.2 g |
| Ethanol | 94.8 ml |

In another embodiment, the base coat composition may include:

| | |
|---|---|
| PEGDA | 4.25 g |
| Ethyl Cellulose 10cP | 0.50 g |
| HPM Cellulose | 0.25 g |
| Irgacure 2959 | 0.2 g |
| DI Water | 20.0 ml |
| Ethanol | 74.8 ml |

The base coat layer may be formed on the surface of a medical device by applying the base coat composition to the surface and then curing and/or drying the base coat composition to form the base coat layer. The base coat compositions may be applied in any suitable manner, such as by dip coating or spraying. The base coat composition may be cured and dried by any suitable manner such as by exposure to UV light.

The concentration of the PEGDA in the base coat layer formed from the base coat composition after drying and curing may be less than 85 wt % of the base coat layer. It may also be less than 50 wt % and, in some embodiments, it may be less than 20 wt % of the base coat layer. For example, the base coat layer formed from the composition after drying and curing may include PEGDA in an amount of between about 5 wt % and about 90 wt % of the base coat layer and a film forming polymer in an amount of about 10 wt % and about 95 wt %. In one embodiment, the base coat layer may include PEGDA in an amount between about 80 wt % and about 90 wt % of the base coat layer and the film forming polymer in an amount of between about 10 wt % and about 20 wt % film forming polymer.

Figure 11:
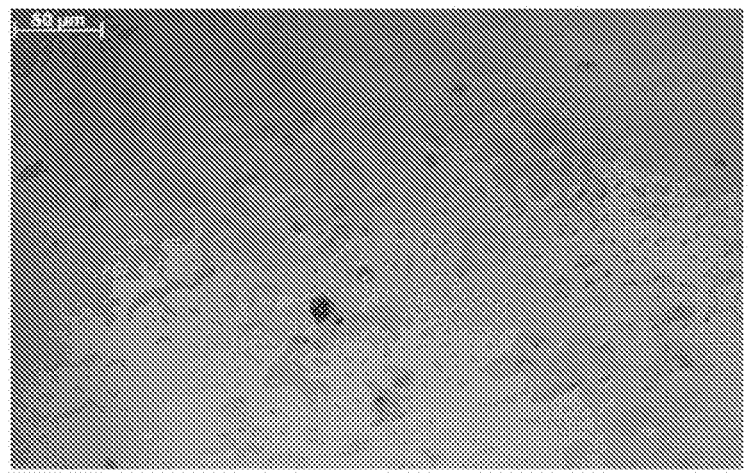
FIG. 11 is a micrograph of a surface of the hydrophilic coating of Example 7.

Furthermore, the components of the base coat layer may be immiscible or partially immiscible. In one embodiment, the PEGDA of the base coat layer comprises a discrete, continuous or bi-continuous phase within the coating layer. The base coat layer may include a phase separated morphology wherein the PEGDA forms one phase and the film forming polymer forms another phase. Referring to FIG. 11, which discloses a two-phase morphology from the coating described below in Example 7, the PVP is in a continuous phase and PEGDA is in a discontinuous phase.

In an alternative embodiment of a base coat composition, the base coat may include a hydrophilic polymer and a cellulose based polymer such as carboxymethyl cellulose, methyl cellulose, ethyl cellulose, hydroxyl methylcellulose, hydroxypropyl cellulose, and hydroxypropyl methylcellulose. In this embodiment, there are no diacrylate compounds in the composition.

Turning to top coat or outer layer 28, the top coat layer may be formed from a blend, such as a top coat composition, that is applied over the base coat layer or directly to the surface of the catheter tube 12 and then cured to form the top coat layer and the hydrophilic coating.

In one embodiment of the top coat composition, the composition may include a water-soluble high molecular weight polymer, such as a hydrophilic polymer, and any of the PEGDA of different Mn described above. These components may be dissolved and/or dispersed in a solvent. The top coat composition may also, optionally, include one or more of curing agents, polyelectrolytes, humectants, plasticizers and/or antioxidants.

The solvent may be any suitable solvent, such as ethanol, methanol, water, isopropyl alcohol or mixtures thereof. Additionally, the PEGDA may have a Mn of less than 1000, or less than 900 or less than 600, or between about 200 and about 600, or between about 400 and about 600.

When used in the top coat composition, the polyelectrolytes may be, for example, a copolymer with acrylic acid, preferably with acrylamide. The polyelectrolyte may be polyacrylic acid-co-acrylamide copolymer (PAAc), polyacrylamide-co-methacrylic acid, or polyacrylic acid. The polyelectrolyte composition may have less than 30% by weight of ionizable groups based on total weight of the copolymer. The humectants or plasticizing agents may be, for example, glycerol or polyethylene glycols or any suitable plasticizer that plasticizes or allows the coating to be more flexible. The curing agent may be a Norrish type I or preferably a Norrish type II photoinitiator, such as benzophenone. The antioxidant may be any suitable antioxidant, such as butyl hydroxytoluene-alcohol (BHT-alcohol).

In one embodiment, the solid components of the top coat composition in the dry state (without solvent) may include PEGDA in an amount of between about 1 wt % and about 20 wt % of the total solids, a hydrophilic polymer(s) in an amount of between about 80 wt % and about 98 wt % and a curing agent in an amount of about 0.05 wt % and about 0.5 wt %. The top coat composition in the dry state may also include an antioxidant in an amount of between about 0.05 wt % and about 0.5 wt % of the total solids, a plasticizer in an amount of between about 2 wt % and about 15 wt %, an polyelectrolyte in an amount of between about 1 wt % and about 10 wt %, and/or any other suitable additive. In other embodiments, the solid components in the dry state may include PEGDA in an amount between about 3 wt % and about 6 wt % of the total solids and a film forming polymer(s) in an amount between about 85 wt % and about 90 wt %, and optionally, an amount of antioxidant, plasticizer, polyelectrolyte and/or any other suitable additive up to 10 wt %.

The top coat composition in the liquid state may include between about 2 wt % and about 10 wt % hydrophilic polymer, between about 0.1 wt % and about 0.6 wt % PEGDA, between about 0.005 wt % and about 0.1 wt % curing agent, and between about 89 wt % and about 97.5 wt % solvent. The top coat composition may, optionally, further include between about .005 wt % and about 0.1 wt % antioxidant, between about 0.1 wt % and about 1 wt % plasticizers and/or about 0.1 wt %, about 1 wt % polyelectrolyte and/or any other suitable additive. In another embodiment the top coat in the liquid state may include between 4 wt % and 7 wt % hydrophilic polymer, between 0.2 wt % and 0.4 wt % PEGDA between about 0.005 wt % and 0.015 wt % curing agent and about 90 wt % to 95 wt % solvent and optionally, an amount of antioxidant, plasticizer, polyelectrolyte and/or any other suitable additive.

The top coat composition may be applied over the base coat layer or directly to the surface of the medical device in any suitable manner, such as by dip coating or spraying. The top coat composition may then be cured in any suitable manner to form the top coat layer and the hydrophilic coating. For example, curing of the top coat composition may include curing by exposure to UV light.

In one embodiment, the dried and/or cured top coat layer formed from the composition may include about 80 wt % to about 95.5 wt % water-soluble high molecular weight polymer and about 0.5 wt % to about 20 wt % PEGDA. The top coat layer may optionally include about 1 wt % to about 10 wt % plasticizer and/or about 1 wt % to about 10 wt % polyelectrolyte. In one embodiment, the top coat layer may include hydrophilic polymer in an amount between about 94 wt % to about 98 wt % hydrophilic polymer, PEGDA in an amount between about 2 wt % to about 6 wt % and, optionally, an amount of antioxidant, plasticizer, polyelectrolyte and/or any other suitable additive.

Figure 9:
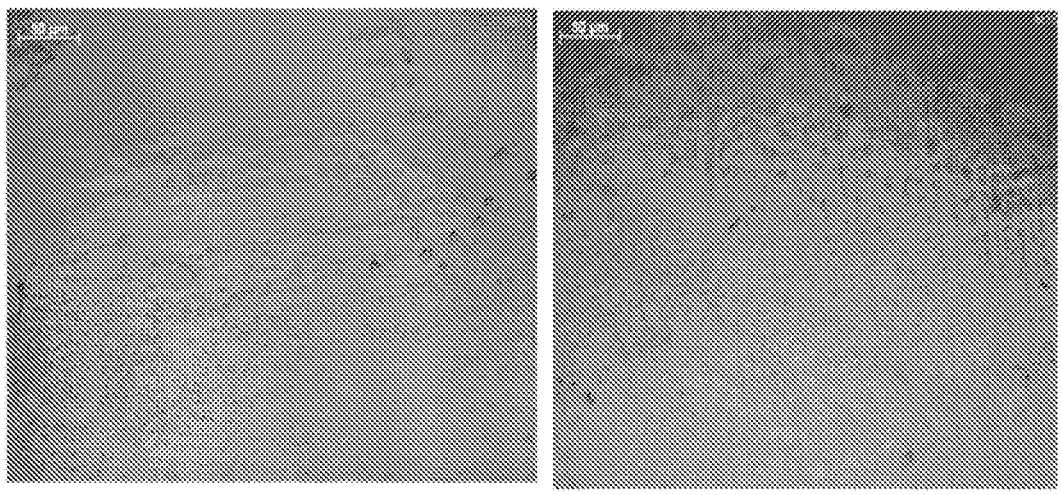
FIG. 9 are micrographs of the surface of hydrophilic coating of Example 6.

The components of the top coat layer may be immiscible or partially immiscible. For example, the PEGDA of the top coat layer may be a partially immiscible or an immiscible component. In one embodiment, the PEGDA of the top coat layer comprises a discrete, continuous or bi-continuous phase within the coating layer. The top coat layer may include a multiple phase morphology wherein the PEGDA separates from the hydrophilic polymer phase during drying and curing. That is, wherein the PEGDA forms one phase and the hydrophilic polymer forms a second phase. FIG. 9 shows a micrograph of the top coat formed from Example 6. As shown in the micrograph, separation of components during drying and curing is evident.

To form the lubricious hydrophilic coating on a substrate, such as a medical device, the base coat composition, when one is used, is applied to a surface of the substrate, by for example, dip coating, spraying or any other suitable manner. The base coat is then cured and/or dried by, for example, UV lights or any other suitable manner. In one embodiment, curing and drying the base coat composition results in a base coat layer having a multiple-phase morphology. The top coat composition is then applied over the base coat layer, when one is used, or applied directly to the surface of the substrate by, for example, dip coating, spraying or any other suitable manner. The top coat composition is then cured and/or dried to form the top coat layer. Curing and/or drying can be done by, for example, exposure to UV light or any other suitable manner. In one embodiment, curing and/or drying of the top coat composition results in a top coat having phase separated components.

When the coating is formed, the substrate may be packaged in a dry or wet environment and optionally radiation sterilized by, for example, gamma or E-beam radiation. When packaged in a dry environment, the substrate, such as a catheter, is placed and sealed in a package without adding any wetting fluid. If packaged and sterilized in a dry environment, a water burstable pouch may be included in the package. This water pouch may be burst after sterilization during manufacturing, or by the user just prior to use. If sterilized in a wet state, the catheter may be packaged with a wetting fluid in direct contact with the hydrophilic coating. The wetting fluid may optionally contain a hydrophilic polymer that protects the hydrophilic coating during radiation. Medical devices which have been coated with the hydrophilic coating disclosed herein may be packaged and radiation sterilized in a wet or dry environment.

The lubricious hydrophilic coatings disclosed herein are coatings that become slippery when wetted with a wetting fluid, such as water. The coatings disclosed herein may a range of CoFs. The desired CoF or lubricity of a coating depends of the intended use of the device. For example, in one embodiment of the coating disclosed herein, the lubricious hydrophilic coating has a coefficient of friction of less than about 0.05 when measured by the procedure set forth in Example 1. The hydrophilic coatings may also have a CoF of less than 0.05 after being abraded or after drying-out for 10 minutes as described below in Example 1. Having a CoF of less than 0.05 may be desirable in the field of urinary catheterization. Higher CoF may still be suitable for use in catheterization, but lower CoFs are desirable for the comfort of the user. In other fields, however, a CoF greater than 0.05 may provide acceptable lubricity.

In one embodiment of a catheter assembly disclosed herein, the assembly is a ready-to-use catheter assembly that includes a packaged sterilized catheter wherein the catheter includes a hydrophilic coating and is packaged in a wet environment (liquid or vapor). The catheter also has a CoF of less than 0.05 immediately after it is removed from the package.

All of the base coats disclosed herein may be used with all of the top coats disclosed herein to form a hydrophilic coating. The base coats, top coats and coating disclosed herein may be applied and used on a variety of substrates, including but not limited to, substrates at least partial formed from one or more of thermoplastic polyolefins, polyvinyl chloride), thermoplastic elastomers, and thermoplastic polyurethanes.

EXAMPLES

Example 1

Hydrophilic coatings were formed on the outer surfaces of catheters made from polyvinyl chloride (PVC catheters). The catheters had a size of CH14 and a shore hardness of 82 A. The hydrophilic coatings included a base coat layer formed on the outer surface of the catheter and a top coat layer formed over the base coat layer. The base coat composition was prepared as indicated below. The base coat composition was applied to the outer surface of each of the catheters and then cured and dried to form a base coat thereon.

The base coat composition included the following components:

| Base Coat | |
| --- | --- |
| Component | Amount |
| Methanol | 97.98% (w/w) |
| Polyvinylpyrrolidone K90 (PVP) (Ashland) | 1.61% (w/w) |
| Irgacure 2959 (BASF) | 0.01% (w/w) |
| Polyethylene glycol diacrylate (PEG400DA) (SR344, Sartomer, inhibitor removed) | 0.40% (w/w) |

The base coat composition was prepared by slowly adding the PVP to methanol while mixing until the PVP was dissolved. PEG400DA and Irgacure 2959 were then added and allowed to fully dissolve while the solution was stirred.

Four top coat compositions also were prepared as indicated below, wherein each of the catheters had one of the four top coat compositions applied over the base coat layer. The top coat compositions were then cured and dried to form a hydrophilic coating on the outer surface of the catheter. The components of each of these top coat compositions were the same, except that each composition included a polyethylene glycol diacrylate of a different number average molecular weight (Mn).

Each of the formulations of the four top coat compositions included one of the following PEGDAs:

| PEGDA | Physical state |
| --- | --- |
| PEGDA Mn250(Sigma Aldrich)) | Low viscosity liquid |
| PEGDA Mn700(Sigma Aldrich) | Low viscosity liquid |
| PEGDA Mn1000(Sigma Aldrich) | Wax (will cold flow) |
| PEGDA Mn6000(Sigma Aldrich) | Heavy wax |

The formulations of the top coat compositions were as follows:

| Top Coats | | | | |
| --- | --- | --- | --- | --- |
| | Top Coat 1-1 | Top Coat 1-2 | Top Coat 1-3 | Top Coat 1-4 |
| PEGDA | 0.30% (w/w) PEGDA 250 | 0.30% (w/w) PEGDA 700 | 0.30% (w/w) PEGDA 1000 | 0.30% (w/w) PEGDA 6000 |
| Ethanol (absolute) | 79.01% (w/w) | 79.01% (w/w) | 79.01% (w/w) | 79.01% (w/w) |
| De-ionized water | 13.97% (w/w) | 13.97% (w/w) | 13.97% (w/w) | 13.97% (w/w) |
| PVP K90 (Ashland) | 5.95% (w/w) | 5.95% (w/w) | 5.95% (w/w) | 5.95% (w/w) |
| BHT-A (Sigma Aldrich) | 0.01% (w/w) | 0.01% (w/w) | 0.01% (w/w) | 0.01% (w/w) |
| Glycerol | 0.74% (w/w) | 0.74% (w/w) | 0.74% (w/w) | 0.74% (w/w) |
| Benzophenone | 0.01% (w/w) | 0.01% (w/w) | 0.01% (w/w) | 0.01% (w/w) |

Each of the top coat compositions were prepared by adding PVP to the ethanol and water and mixing until dissolved. The remaining components (glycerol, PEGDA, BHT-A and benzophenone) were then added and allowed to fully dissolve under stirring.

To form the hydrophilic coating on the outer surfaces of each of the catheters, the catheters were immersed in the base coat composition for a period of 10 seconds and then withdrawn at a rate of 0.7 cm/sec using a Harland PDX coating machine containing UV lamps. The base coat composition was then cured and dried under UV lamps for 45 seconds to form a base coat layer covering the outer surface of the catheter. The catheters were then immersed into one of the four top coat compositions for 10 seconds and withdrawn at a rate of 0.5 cm/sec. The top coat composition was then UV cured and dried under UV lamps for 10 minutes to form the top coat layer resulting in the formation of a hydrophilic coating on the catheter.

The catheters of each of the top coat formulations (1-1, 1-2, 1-3 and 1-4) were divided into two groups—those of which that were packaged and sterilized in a dry state ("dry sterilized") and those that were packaged and sterilized in a hydrated state ("wet sterilized").

The "dry sterilized" catheters were individually packaged and sealed in dry foil pouches (i.e., no water or wetting fluid added to the package). The "dry sterilized" catheters were then gamma sterilized in the package at 30-35 kGy. The "wet sterilized" catheters were immersed and force hydrated in water for 30 seconds and then individually packaged and sealed in a foil pack containing 8 mL of water in a gas permeable, liquid impermeable water reservoir. Once the catheter was placed inside of the foil pack, the foil pack was sealed. The liquid water remained in the gas permeable reservoir, such that the liquid water did not come into contact with the coating. The liquid water produced water vapor that formed a humid atmosphere in the package. Packages of this type are currently used for vapor hydrating catheters, such as in Hollister's VaPro® vapor hydrated catheter products. The "wet sterilized" catheters were then gamma sterilized in the package at a dose of about 30-35 kGy.

After sterilization, the initial, abraded and ten minute dry-out coefficients of friction (CoFs) of each of the catheters was measured with the hydrophilic coating in a hydrated state. For testing the CoFs of the "dry sterilized" catheters, the catheters were removed from their packages and immersed in water for 30 seconds to achieve a hydrated state. The "wet sterilized" catheters were in a hydrated state upon removal from the package.

The CoF measurements are an indicator of lubricity and were measured using a Harland Friction Tester Model FTS5500, The CoFs of the catheters were determined by inserting a mandrel into 127 mm section of the coated catheter tube. The tube was then clamped between two pieces of silicone rubber at 100 g load wherein the silicone rubber had a shore hardness of 60 A. The catheter tube with the mandrel inserted therein was pulled through the two pieces of silicone rubber at a speed of 10 mm/s. The force required to pull about 80 mm of the catheter tube through the two pieces of silicone rubber was measured. The CoF value was calculated from the ratio of recorded to applied loads (i.e., the recorded load divided by the applied load) when steady state was reached. The CoF of each type of catheter was measured immediately after hydration for the "dry sterilized" catheters or after removal from the package for the "wet sterilized" catheters ("initial"), immediately after being abraded ("abraded") and immediately after a ten-minute dry-out time ("dry-out").

In measuring the abraded CoFs, the catheter, with the hydrophilic coating in a hydrated state, was cycled back and forth 25 times through a hole in a 1 mm thick, silicone pad having a shore hardness of 60 A. The hole was just smaller than the outer diameter of the catheter tube and the abrasion took place under water. Abrading the catheter in this fashion is designed to remove any portions of the coating that is not well adhered to the tubes. After abrasion, the CoF was measured as described above.

In measuring the ten minute dry-out time CoF, the catheter, immediately after hydration for "dry sterilized" catheter or immediately after removal from the package for "wet sterilized" catheters, was placed in an atmosphere having a temperature of 23° C. and a relative humidity of 50% for 10 minutes before measuring the CoF.

Example 1

Results

Table 1 shows the average CoFs for the initial, abraded and dry-out tests for "dry sterilized" and "wet sterilized" catheters coated with top coats 1-1, 1-2, 1-3 and 1-4.

TABLE 1

| | Dry Sterilized CoF | | | Wet Sterilized CoF | | |
|---|---|---|---|---|---|---|
| Top Coat | Initial Avg. | Abraded Avg. | 10 Min Dry-out Avg. | Initial Avg. | Abraded Avg. | 10 Min Dry-out Avg. |
| 1-1 | 0.0149 | 0.0151 | 0.0277 | 0.0096 | 0.0128 | 0.0225 |
| 1-2 | 0.0083 | 0.0111 | 0.0182 | 0.0073 | 0.0112 | 0.0430 |
| 1-3 | 0.0075 | 0.0087 | 0.0118 | 0.0194 | 0.0502 | 0.4384 |
| 1-4 | 0.0091 | 0.0134 | 0.0126 | 0.0294 | 0.1300 | 0.4798 |

As can be seen from the above results, top coats 1-1 (PEGDA Mn250) and 1-2 (PEGDA Mn700), exhibited lower "wet sterilized" CoFs for initial, abraded and 10 minute dry out measurements than top coats 1-3 (PEGDA Mn1000) and 1-4 (PEGDA Mn6000). Furthermore, the abraded and 10 minute dry out CoFs of top coats 1-1 and 1-2 were significantly lower than those of top coats 1-3 and 1-4.

Dye uptake tests were conducted on the catheters to assess the level of adhesion/non-adhesion between the hydrophilic coatings and catheters. After the CoFs of the abraded catheters were measured, the catheters were dried-out (dehydrate). The dried-out catheters were then immersed in a water soluble red dye for 2 minutes. The catheters were then visually inspected to determine if the dye had been uniformly taken up throughout the coating or if sections of the coated portion of the catheter were dye-free. A uniform dye uptake throughout the coated portion of the catheter indicates that the hydrophilic coating has good adhesion to the catheter. If the coated portion of the catheter has undyed sections, this is an indication that the hydrophilic coating or sections thereof have significantly thinned and/or separated from the catheter due to lack of adhesion to the catheter.

Figure 4:
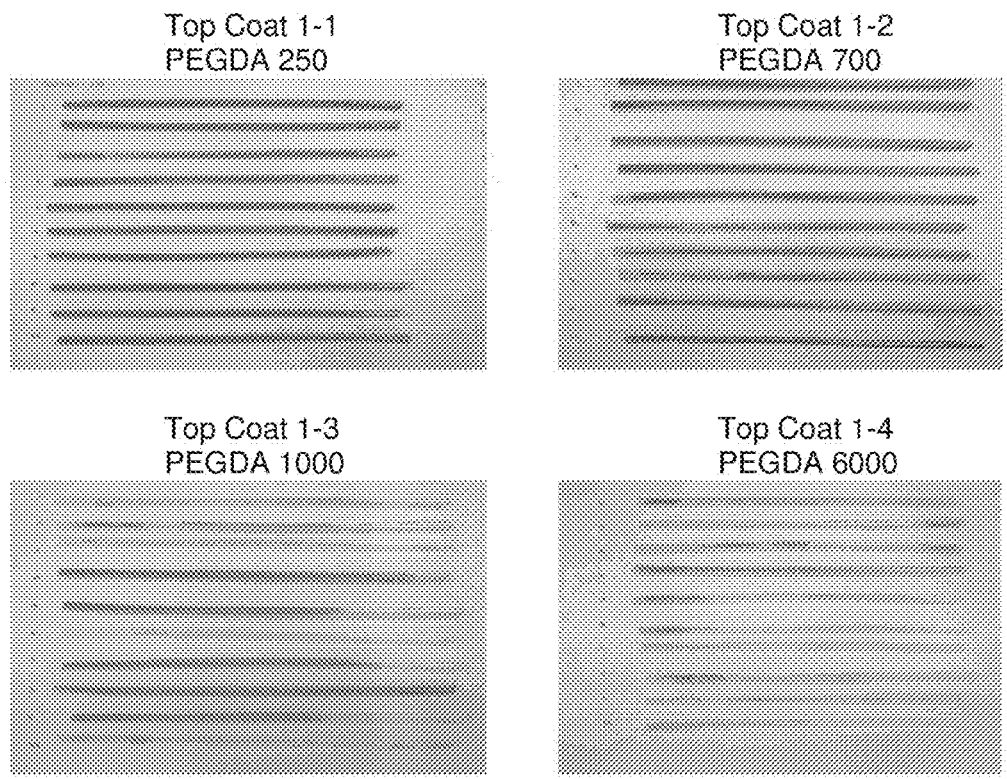
FIG. 4 are photographs of catheter tubes showing the visual results of the dye tests of Example 1.

FIG. 3 shows the results of dye test conducted on the abraded "dry sterilized" catheters having hydrophilic coatings formed from top coats 1-1, 1-2, 1-3 and 1-4, and FIG. 4 shows the results of dye tests conducted on the abraded "wet-sterilized" catheters having hydrophilic coatings formed from top coats 1-1, 1-2, 1-3, and 1-4.

A visual inspection of the "dry sterilized" and "wet sterilized" catheters including hydrophilic coatings formed from top coats 1-1 and 1-2 showed that the hydrophilic coatings exhibited uniform dye uptake which is an indication that the hydrophilic coating had strong adhesion to the catheter and good coating cohesion. A visual inspection of the "dry sterilized" and "wet sterilized" catheters including a hydrophilic coating formed from top coats 1-3 and 1-4 showed that some of the "dry sterilized" catheters and all of the "wet sterilized" catheters exhibited undyed and/or weakly dyed portions, which are indications that the hydrophilic coatings formed from top coats 1-3 and 1-4 had a lower level of adhesion to the catheter and showed significant thinning.

Example 2

In Example 2, hydrophilic coatings were formed on the outer surfaces of PVC catheters having a size of CH14 and a shore hardness of 82 A. The hydrophilic coatings were formed from a base coat layer and a top coat layer. The base coat composition was prepared as indicated below and was applied to each of the catheters to form a base coat layer on the outer surface of the catheter. Additionally, the top coat composition was prepared as indicated below and applied over the base coat layer to form the hydrophilic coating on the catheter.

The formulation of the base coat composition included the following components:

| Base Coat | |
|---|---|
| Component | Amount (w/w) |
| Methanol | 97.98% (w/w) |
| PVP K90 (Ashland) | 1.61% (w/w) |
| Irgacure 2959 (BASF) | 0.01% (w/w) |
| PEG400DA (SR344, Sartomer, inhibitor removed) | 0.40% (w/w) |

The base coat composition was prepared by slowly adding PVP to methanol while mixing until the PVP was dissolved. PEG400DA and Irgacure 2959 were then added and allowed to fully dissolve while the composition was stirred.

The formulation of the top coat composition included the following components:

| Top Coat | |
|---|---|
| Component | Amount (w/w) |
| Ethanol (absolute) (Lennox) | 78.99% (w/w) |
| De-ionized water (Lennox) | 14.00% (w/w) |
| PVP K90 (Ashland) | 5.95% (w/w) |

Top Coat

| Component | Amount (w/w) |
| --- | --- |
| BHT-A (Sigma Aldrich) | 0.01% (w/w) |
| PEG400DA (SR344, Sartomer, inhibitor removed) | 0.30% (w/w) |
| Glycerol | 0.74% (w/w) |
| Benzophenone | 0.01% (w/w) |

The top coat composition was prepared by adding PVP to the ethanol and water and mixing until dissolved. The remaining components (glycerol, PEG400DA, BHT-A, and benzophenone) were then added and allowed to fully dissolve under stirring.

To form the hydrophilic coating on the outer surfaces of the catheters, the catheters were immersed in the base coat composition for a period of 10 seconds and then withdrawn at a rate of 0.7 cm/sec using a Harland PDX coating machine containing UV lamps. The base coat composition was then cured and dried under UV lamps for 45 seconds to form a base coat layer on the outer surface of the catheter. The catheters were then immersed in the top coat composition for 10 seconds and withdrawn at a rate of 0.5 cm/sec. The top coat composition was then UV cured and dried under UV lamps for 10 minutes to form the top coat layer, (resulting in the formation of the hydrophilic coating on the catheter.

After the hydrophilic coating was formed on each of the catheters, the catheters were individually packaged and sealed in a foil pack containing 8 mL of water in a gas permeable, liquid impermeable water reservoir, as described above in Example 1. Ten (10) days after packaging, the packaged catheters were gamma sterilized in the package at a dose of about 30-35 kGy.

After sterilization, each catheter was removed from its package and immersed in water for 30 seconds. The initial, abraded and ten minute dry-out coefficients of friction of each of the catheters was measured in accordance with the procedures described above in Example 1.

Example 2

Results

Table 2 shows the average CoFs for the initial, abraded and dry-out measurements.

TABLE 2

| Initial Avg. | Abraded Avg. | 10 Min Dry-out Avg. |
| --- | --- | --- |
| 0.010 | 0.012 | 0.027 |

As shown by this data the average initial, abraded and dry-out CoFs were all less than 0.05.

Figure 5:
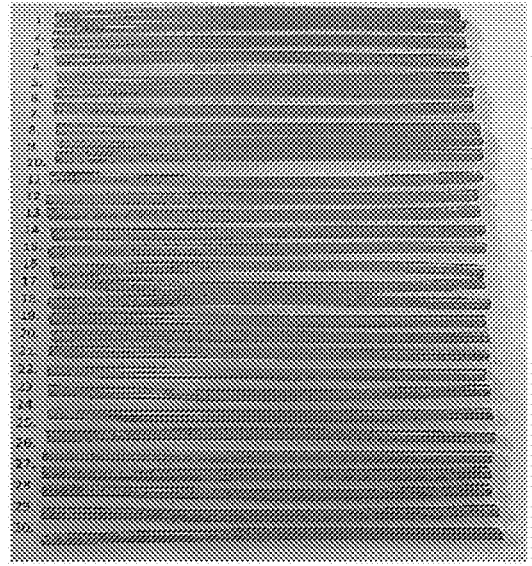
FIG. 5 is a photograph of catheter tubes showing the visual results of the dye test of Example 2.

Dye tests were conducted on the abraded catheters of Example 2 in accordance with the methods described above in Example 1. The results of dye test are shown in FIG. 5. As shown in this figure, the hydrophilic coating of Example 2 exhibited uniform dye uptake, which is an indication that the hydrophilic coating had strong adherence to the catheter and good cohesion.

Example 3

The hydrophilically coated catheters of Example 3 were coated with the same base and top coats as described in Example 2 and by the same coating procedures. The hydrophilic coated catheters were immersed in water for 30 seconds and then sealed in foil packages containing 10 ml of loose water. Four weeks after packaging, the catheters were E-beam sterilized in their packages at a dose of 40 kGy. After sterilization, the packaged catheters were subjected to an accelerated aging process in which the catheters were stored in an oven at 40° C. for seven weeks to simulate six months of real time aging. After being subjected to the accelerated aging process, the initial, abraded and 10 minute dry-out CoFs were measured using the procedures as described above in Example 1.

Example 3

Results

Table 3 shows the average CoF initial, abraded and dry-out measurements of the catheters of Example 3.

TABLE 3

| Initial Avg. | Abraded Avg. | 10 Min Dry-out Avg. |
| --- | --- | --- |
| 0.048 | 0.047 | 0.198 |

The average initial and abraded CoF measurements were lower than the average ten minute dry-out measurement. It is believed that the higher CoFs of the ten minute dry-out samples were due to overcuring of the hydrophilic coating from the combination of the curing process and E-beam sterilization. It is believed that the curing process and E-beam sterilization can be adjusted to produce lower CoFs in the ten minute dry-out samples.

Figure 6:
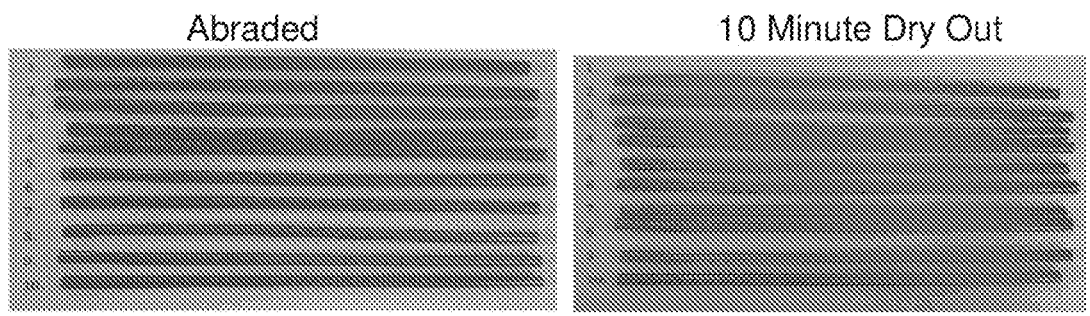
FIG. 6 are photographs of catheter tubes showing the visual results of the dye tests of Example 3.

Dye tests were conducted in accordance with the procedures described above in Example 1. These dye tests were conducted on the abraded catheters and the catheters subjected to the ten minute dry-out test. The results of dye test are shown in FIG. 6. As shown in this figure, the hydrophilic coating of Example 3 exhibited uniform due uptake, which is an indication of good adhesion to the catheter and good cohesion of the sterilised coating.

Example 4

The hydrophilic coatings formed on the catheters of Example 4 were formed from the same top and base coat compositions using the same procedures described above in Example 2. The hydrophilic coated catheters were immersed in water for 30 seconds and then were sealed in foil packages containing 10 ml of loose water. Four weeks after packaging, the catheters were E-beam sterilized in their packages at a dose of 40 kGy. Two days after sterilization, the catheters were removed from their packages and the initial, abraded and ten minute dry-out CoFs were measured using the procedures as described above in Example 1.

Example 4

Results

Table 4 shows the average initial, abraded and dry-out CoF measurements of the catheters of Example 2.

TABLE 4

| Initial Avg. | Abraded Avg. | 10 Min Dry-out Avg. |
| --- | --- | --- |
| 0.028 | 0.059 | 0.239 |

Figure 7:
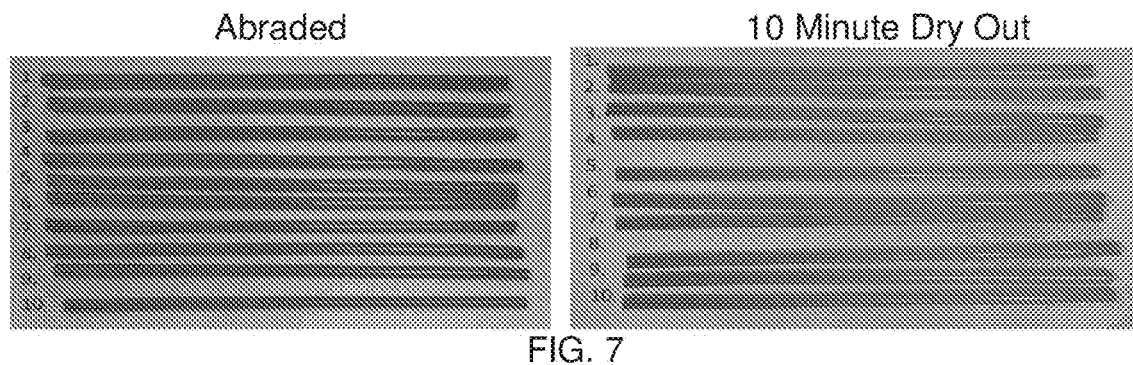
FIG. 7 are photographs of catheter tubes showing the visual results of the dye test of example 4.

Dye tests, in accordance with the procedures of Example 1, were conducted on the abraded and 10 minute dry-out samples. The results of the dye tests are shown in FIG. 7. A visual inspection of the catheters showed uniform dye uptake which indicates that the coating had good adhesion to the catheter and good coating cohesion.

Example 5

In Example 5, hydrophilic coatings were formed on the outer surfaces of PVC catheters having a size of CH14 and a shore hardness of 82 A. The hydrophilic coatings were formed from the same base coat layers as described in Example 2 and one of the below listed top coats layers. The base coat composition was prepared as described above in Example 2.

The top coat compositions were prepared as described below.

| | Top Coat | | | |
|---|---|---|---|---|
| | Top Coat 5-1 | Top Coat 5-2 | Top Coat 5-3 | Top Coat 5-4 |
| PVP K90 (Ashland) | 5.71% (w/w) | 5.71% (w/w) | 6.51% (w/w) | 6.51% (w/w) |
| PEGDA Mn400 (SR344, Sartomer, inhibitor removed) | 0.12% (w/w) | 0.12% (w/w) | 0.14% (w/w) | 0.14% (w/w |
| Glycerol | 0.59% (w/w) | 0.59% (w/w) | 0.68% (w/w) | 0.68% (w/w) |
| Benzophenone | 0.01% (w/w) | 0.01% (w/w) | 0.01% (w/w) | 0.01% (w/w) |
| BHT-A Sigma Aldrich) | 0.01% (w/w) | 0.01% (w/w) | 0.02% (w/w) | 0.02% (w/w) |
| Ethanol (absolute) (Lennox) | 84.77% (w/w) | 0% (w/w) | 92.65% (w/w) | 0% (w/w) |
| Methanol | 0% (w/w) | 84.77% (w/w) | 0% (w/w) | 92.65% (w/w) |
| De-ionized water (Lennox) | 8.78% (w/w) | 8.78% (w/w) | 0% (w/w) | 0% (w/w) |

Each of the top coat compositions were prepared by adding PVP to the solvent(s) (ethanol, methanol and/or water) and mixing until dissolved. The remaining components (glycerol, PEGDA, BHT-A, and benzophenone) were then added and allowed to fully dissolve. The dried coatings all contain the same general composition. That is, the amount of and ratio of the components of the top coat layers formed were generally the same. The main difference was the choice of solvent and the presence of water or not in the formulation.

To form the hydrophilic coating on the outer surfaces of the catheters, the catheters were immersed in the base coat composition for a period of 10 seconds and then withdrawn at a rate of 0.7 cm/sec using a Harland PDX coating machine containing UV lamps. The base coat composition was then cured and dried under UV lamps for 45 seconds to form a base coat layer covering the outer surface of the catheter. The catheters were then immersed in one of top coat compositions for 10 seconds and withdrawn at a rate of 0.5 cm/sec. The top coat composition was then UV cured and dried under UV lamps for 10 minutes to form the top coat layer, resulting in a hydrophilic coating on the catheter.

The coated catheters of each of the top coat formulations were divided into two groups—those of which that would be packaged and "dry sterilized" and those that would be packaged and "wet sterilized".

The catheters that were "dry sterilized" were individually packaged and sealed in dry foil pouches (i.e., no water or wetting fluid added to the package). The "dry sterilized" catheter were then gamma sterilized in the package at 30-35 kGy. The catheters that were "wet sterilized" were immersed in water for 30 seconds and then individually packaged and sealed in a foil pack containing 8 mL of water in a gas permeable, liquid impermeable water reservoir, as described above in Example 2. The wet sterilised catheters were then gamma sterilized in the package at a dose of about 30-35 kGy.

The initial, abraded and ten minute dry-out coefficients of friction (CoFs) of each of the sterilized catheters was measured with the hydrophilic coating in a hydrated state. To measure the CoFs of the "dry sterilized" catheters, the catheters were removed from their packages and were immersed in water for 30 seconds to achieve a hydrated state. The "wet sterilized" catheters were in a hydrated state upon removal from the package. The initial, abraded and ten minute CoFs were measured using the same procedures as described above in Example 1.

Example 5

Results

Table 5 shows the average initial, abraded and dry-out CoF measurements for "dry sterilized" and "wet sterilized" catheters coated with top coats.

TABLE 5

| | Dry Sterilized CoF | | | Wet Sterilized CoF | | |
|---|---|---|---|---|---|---|
| Top Coat | Initial Avg. | Abraded Avg. | 10 Min Dry-out Avg. | Initial Avg. | Abraded Avg. | 10 Min Dry-out Avg. |
| 5-1 | 0.012 | 0.014 | 0.021 | 0.018 | 0.031 | 0.3 |
| 5-2 | 0.01 | 0.018 | 0.019 | 0.062 | 0.39 | >0.8 |
| 5-3 | — | — | — | 0.054 | >0.8 | >0.8 |
| 5-4 | — | — | — | >0.8 | >0.8 | >0.8 |

As can be seen from these results, the hydrophilic coatings formed from top coat compositions 5-1 and 5-2 (both of which included water) exhibited lower CoFs in the "dry sterilized" samples and top coat 5-1 also exhibited lower CoFs in the "wet sterilized" samples. In contrast, the hydrophilic coatings formed from the top coat formulations without water, 5-3 and 5-4, exhibited higher CoFs which fell outside the measurement range of the friction tester, or the coating did not adhere to the catheter, in which case the catheter could not be tested.

Figure 8:
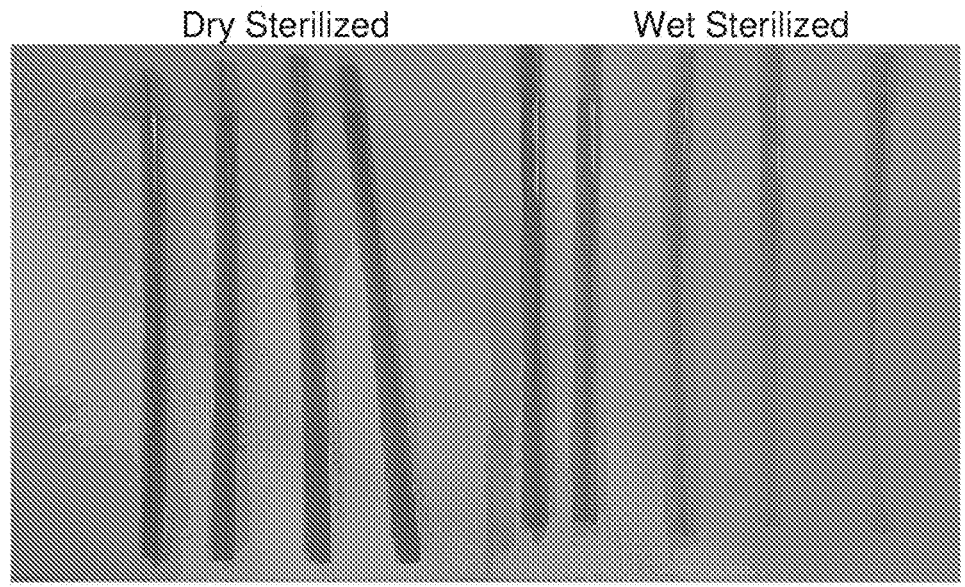
FIG. 8 are photographs of catheter tubes showing the visual results of the dye test of Example 5.

FIG. 8 shows the results of dye test conducted on the abraded "dry sterilized" and "wet sterilized" catheters that included the hydrophilic coating formed from top coat composition 5-1, A visual inspection of the catheters showed uniform dye uptake which indicates that the coating had strong adhesion to the catheter and maintained good cohesion. Samples 5-3 and 5-4 had no dye retention indicating coating degradation in the hydrated sterilisation process.

Example 6

In Example 6, hydrophilic coatings were formed on the outer surfaces of PVC catheters. The hydrophilic coatings were formed from similar base coat compositions as described in Example 2 and one of the below listed top coat compositions.

The formulations of the top coat compositions were prepared as described below.

| Top Coats | | |
|---|---|---|
|  | Top Coat 6-1 | Top Coat 6-2 |
| PVP K90 (Ashland) | 5.70% (w/w) | 5.71% (w/w) |
| PEG400DA (SR344, Sartomer, inhibitor removed) | 0.23% (w/w) | 0.09% (w/w) |
| Glycerol | 0.71% (w/w) | 0.71% (w/w) |
| Benzophenone | 0.01% (w/w) | 0.01% (w/w) |
| Ethanol (absolute) (Lennox) | 84.58% (w/w) | 93.49% (w/w) |
| De-ionized water (Lennox) | 8.77% (w/w) | 0% (w/w) |

Each of the top coat compositions were prepared by adding PVP to the solvent (ethanol or ethanol/water) and mixing until dissolved. The remaining components (glycerol, PEG400DA, and benzophenone) were then added and allowed to fully dissolve.

To form the hydrophilic coating on the outer surfaces of the substrates, the substrates were immersed in the base coat composition for a period of 10 seconds and then withdrawn at a rate of 0.7 cm/sec using a Harland PDX coating machine containing UV lamps. The base coat composition was then cured and dried under UV lamps for 45 seconds to form a base coat layer covering the outer surface of the substrate. The substrates were then immersed in one of top coat compositions for 10 seconds and withdrawn at a rate of 0.5 cm/sec. The top coat composition was then UV cured and dried under UV lamps for 10 minutes to form the top coat layer, resulting in a hydrophilic coating on the substrate.

The catheters were "wet sterilized" wherein they were immersed and force hydrated in water for 30 seconds and then individually packaged and sealed in a foil pack containing 8 mL of water in a gas permeable, liquid impermeable water reservoir. Once the catheter was placed inside of the foil pack, the foil pack was sealed. The liquid water remained in the gas permeable reservoir, such that the liquid water did not come into contact with the coating. The liquid water produced water vapor that formed a humid atmosphere in the package. Packages of this type are currently used for vapor hydrating catheters, such as in Hollister's VaPro® vapor hydrated catheter products. The "wet sterilized" catheters were then gamma sterilized in the package at a dose of about 30-35 kGy.

The catheters were removed from their packages and the initial, abraded and 10 minute dry-out CoFs were measured using the procedures described above in Example 1.

Example 6

Results

Table 6 shows the average initial, abraded and dry-out CoF measurements for "dry sterilized" and "wet sterilized" catheters coated with top coats.

TABLE 6

| | Wet Sterilized CoF | | |
|---|---|---|---|
| Top Coat | Initial Avg. | Abraded Avg. | 10 Min Dry-out Avg. |
| 6-1 | 0.0093 | 0.0152 | 0.0102 |
| 6-2 | 0.0735 | 0.3905 | 0.7509 |

As can be seen from the above results, the top coat layer formed from top coat composition 6-1 has lower CoFs than those formed from top coat composition 6-2.

FIG. 9 shows two micrographs of the outer surface of the hydrophilic coating formed from top coat 6-1 after the top coat layer has been cured and dried. The coating was slightly hazy. As can be seen in the micrographs, the coating displays phase separation of the components. During drying and curing, PEGDA separated out from the PVP film former forming localised domains of PEGDA dispersed within the PVP matrix.

Figure 10:
FIG. 10 is a micrograph of a surface of the hydrophilic coating of Example 6.

FIG. 10 is a micrograph of the outer surface of the hydrophilic coating formed from top coat 6-2 after the top coat has been cured and dried. The coating was clear and as can be seen by this micrograph, the components of the coating do not display obvious separation during drying and curing.

Example 7

A coating including PVP and PEG400DA was prepared as indicated below and coated on a TPU substrate.

The components of the coating composition were as follows:

| Coating | |
|---|---|
| Component | Amount % (w/w) |
| PVP K90 (Ashland) | 1.61 |
| PEG4000A(SR344, Sartomer, inhibitor removed) | 0.40 |
| Irgacure 2959 (BASF) | 0.01 |
| Methanol | 97.98 |

The coating composition was prepared by adding PVP to the methanol and mixing until dissolved. The remaining components (PEG400DA and Irgacure 2959) were then added and allowed to fully dissolve.

To form the hydrophilic coating on the outer surfaces of the substrate, the substrate were immersed in the base coat composition for a period of 10 seconds and then withdrawn at a rate of 0.7 cm/sec using a Harland PDX coating machine containing UV lamps. The base coat composition was then cured and dried under UV lamps for 45 seconds to form a base coat layer covering the outer surface of the substrate. The substrates were then immersed in one of top coat compositions for 10 seconds and withdrawn at a rate of 0.5 cm/sec. The top coat composition was then UV cured and dried under UV lamps for 10 minutes to form the top coat layer, resulting in a hydrophilic coating on the substrate.

FIG. 11 is a micrograph of the surface of the coating. The coating was cloudy and as can be seen in the micrographs, the coating includes a multiple phase morphology wherein the PVP and PEGDA have separated into two distinct phases. During drying and curing, PEGDA separated out from the PVP film former, resulting in a continuous phase of PVP and a discontinuous phase of dispersed domains of cured PEGDA.

Example 8

Figure 12:
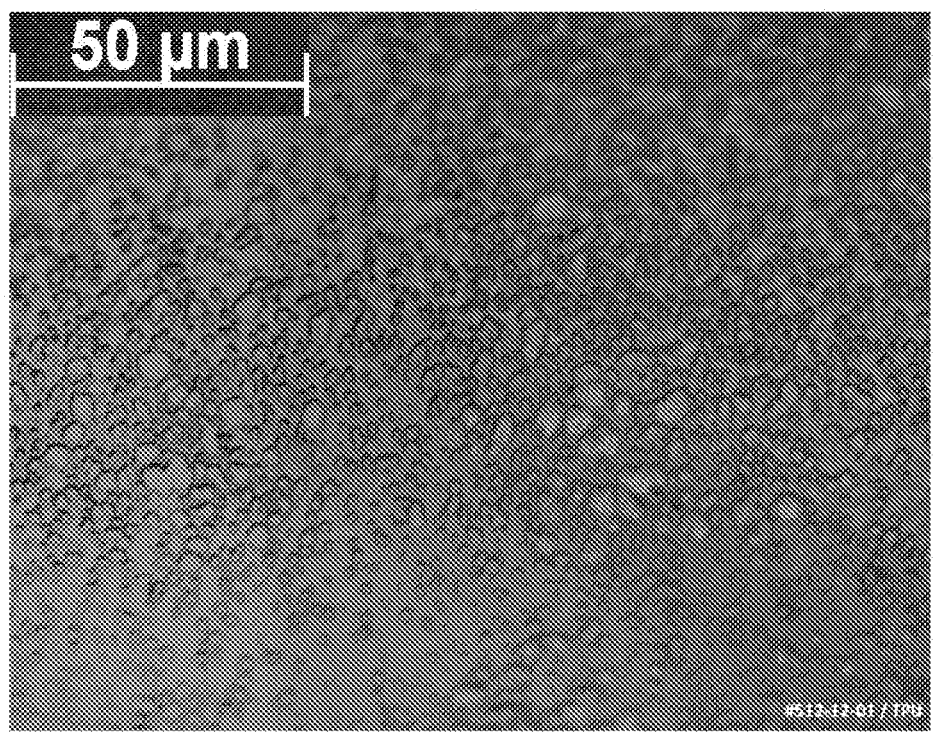
FIG. 12 is a micrograph of a surface of the hydrophilic coating of Example 8.

A coating including a blend of PVP and PEG400DA 400 was cast and cured and dried on a TPU surface. The coating solution was made by dissolving PVP and PEG400DA in ethanol wherein the weight percent between PEG400DA and PUP was 70% (w/w) PEG400DA and 30% (w/w) PUP. The solution was cast onto the surface of a substrate made from TPU and then cured and dried under UV lights. FIG. 12 is a micrograph of the outer surface of the coating. The coating was cloudy and as can be seen in the micrographs, the coating includes a multiple phase morphology wherein the PUP and PEGDA have separated into two phases. During dying and curing, PVP separated out from the PEGDA, resulting in a continuous phase of PEGDA and a discontinuous phase or domains of PVP.

Example 9

Hydrophilic coatings were formed on the outer surfaces of catheters made of thermoplastic elastomers (TPE) and catheters made from PVC. The TPE catheters were supplied by Raumedic and the shore hardness of the catheters was one of 83 A, 87 A or 90 A. The PVC catheters had a shore hardness of 82 A. The hydrophilic coatings were formed from a base coat layer and a top coat layer. The base coat composition was prepared as indicated below and was applied to each of the catheters to form a base coat layer on the outer surface of the catheter. Additionally, the top coat composition included the same components and was prepared in the same manner as described above in Example 2. The top coat composition was applied over the base coat layer to form the hydrophilic coating on the catheter.

The formulation of the base coat composition included the following components:

| Base Coat | |
|---|---|
| Component | Amount (w/w) |
| Ethanol | 93.50% |
| PVP K90 | 0.94% |
| Irgacure 2959 (BASF) | 0.25% |
| PEG4000A (SR344, Sartomer, inhibitor removed) | 5.31% |

The base coat composition was prepared by slowly adding PVP to ethanol while mixing until the PUP was dissolved. PEG400DA and Irgacure 2959 were then added and allowed to fully dissolve while the solution was stirred.

To form the hydrophilic coating on the outer surface of each of the different types of catheters, the catheters were immersed in the base coat composition for a period of 10 seconds and then withdrawn at a rate of 0.7 cm/sec using a Harland PCX coating machine containing UV lamps. The base coat composition was then cured and dried under UV lamps for 45 seconds to form a base coat layer covering the outer surface of the catheter. The catheters were then immersed in the top coat composition for 10 seconds and withdrawn at a rate of 0.5 cm/sec. The top coat composition was then UV cured and dried under UV lamps for 10 minutes to form the top coat layer, resulting in the formation of a hydrophilic coating on the catheter.

The coated catheters of each catheter type were divided into two groups—non-sterilized catheters and sterilized catheters.

The non-sterilized catheters were immersed in water for 30 seconds and the initial and abraded CoFs were measured immediately thereafter. The sterilized catheters were "dry sterilized" in that they were individually packaged and sealed in dry foil pouches (i.e., no water or wetting fluid added to the package), and then gamma sterilized in the package at 30-35 kGy. The dry sterilized catheters were removed from their packages and immersed in water for 30 seconds prior to measure the initial and abraded CoFs. The CoFs were measured in the same manner as described above in Example 1.

Example 9

Results

Table 7 shows the initial and abraded CoFs for each of the different catheters having the hydrophilic coating thereon.

TABLE 7

| | Non-Sterilized | | Sterilized | |
|---|---|---|---|---|
| Catheter | CoF Initial Avg. | CoF Abraded Avg. | CoF Initial Avg. | CoF Abraded Avg. |
| TPE 83A | 0.021 | 0.021 | 0.021 | 0.026 |
| TPE 87A | 0.031 | 0.024 | 0.027 | 0.030 |
| TPE 90A | 0.030 | 0.028 | 0.028 | 0.030 |
| PVC 82A | 0.030 | 0.024 | 0.014 | 0.025 |

Example 10

Hydrophilic coatings were formed on the outer surfaces of catheters made of thermoplastic elastomers (TPE) and catheters made from PVC. The TPE catheters were supplied by Raumedic and the shore hardness of the catheters was one of 83 A, 87 A or 90 A. The PVC catheters had a shore hardness of 82 A. The hydrophilic coatings were formed from a base coat layer and a top coat layer. The base coat composition was prepared as indicated below and was applied to each of the catheters to form a base coat layer on the outer surface of the catheter. Additionally, top coat composition included the same components and was prepared as described above in Example 2. The top coat composition was applied over the base coat layer to form the hydrophilic coating on the catheter.

The formulation of the base coat composition included the following components:

| Base Coat | |
|---|---|
| Component | Amount (w/w) |
| Ethanol | 96.64% |
| PVP K90 Fluka | 0.48% |
| Irgacure 2959 (BASF) | 0.13% |
| PEG4000A (SR344, Sartomer, inhibitor removed) | 2.75% |

The base coat composition was prepared by slowly adding PVP to ethanol while mixing until the PVP was dissolved. PEG400DA and Irgacure 2959 were then added and allowed to fully dissolve while the solution was stirred.

To form the hydrophilic coating on the outer surface of each of the different types of catheters, the catheters were immersed in the base coat composition for a period of 10 seconds and then withdrawn at a rate of 0.7 cm/sec using a Harland PCX coating machine containing UV lamps. The base coat composition was then cured and dried under UV lamps for 45 seconds to form a base coat layer covering the outer surface of the catheter. The catheters were then immersed in the top coat composition for 10 seconds and withdrawn at a rate of 0.5 cm/sec. The top coat composition was then UV cured and dried under UV lamps for 10 minutes to form the top coat layer, resulting in the formation of a hydrophilic coating on the catheter.

The coated catheters of each catheter type were divided into two groups—non-sterilized catheters and sterilized catheters.

The non-sterilized catheters immersed in water for 30 seconds and then the initial and abraded CoFs were measured. The sterilized catheters were "dry sterilized" in that they were individually packaged and sealed in dry foil pouches (i.e., no water or wetting fluid added to the package), and then gamma sterilized in the package at 30-35 kGy. The dry sterilized catheters were removed from their packages and immersed in water for 30 seconds prior to measure the initial and abraded CoFs. The CoFs were measured in the same manner as described above in Example 1.

Example 10

Results

Table 8 show the initial and abraded CoFs for each of the different catheters having the hydrophilic coating thereon.

TABLE 8

|  | Non-Sterilized | | Sterilized | |
| --- | --- | --- | --- | --- |
|  | CoF Initial Avg. | CoF Abraded Avg. | CoF Initial Avg. | CoF Abraded Avg. |
| TPE 83A | 0.028 | 0.023 | 0.022 | 0.025 |
| TPE 87A | 0.022 | 0.021 | 0.023 | 0.027 |
| TPE 90A | 0.020 | 0.022 | 0.020 | 0.020 |
| PVC 82A | 0.018 | 0.022 | 0.019 | 0.020 |

Example 11

Hydrophilic coatings were formed on the outer surfaces of catheters made of thermoplastic elastomers (TPE) and catheters made from PVC. The TPE catheters were supplied by Raumedic and the shore hardness of the catheters was one of 83 A, 87 A or 90 A. The PVC catheters had a shore hardness of 82 A. The hydrophilic coatings were formed from a base coat layer and a top coat layer. The base coat composition was prepared as indicated below and was applied to each of the catheters to form a base coat layer on the outer surface of the catheter. Additionally, the top coat composition included the same components and was prepared in the same manner as described above in Example 2. The top coat composition was applied over the base coat layer to form the hydrophilic coating on the catheter.

The formulation of the base coat composition included the following components:

| Base Coat | |
| --- | --- |
| Component | Amount (w/w) |
| Ethanol | 93.50% |
| PVP K90 Fluka | 0.63% |
| Irgacure 2959 (BASF) | 0.25% |
| PEG400DA (SR344, Sartomer, inhibitor removed) | 5.31% |
| Ethyl Cellulose (Sigma Aldrich) | 0.31% |

The base coat composition was prepared by slowly adding PVP to ethanol while mixing until the PVP was dissolved. PEG400DA, Ethyl Cellulose and Irgacure 2959 were then added and allowed to fully dissolve while the solution was stirred.

To form the hydrophilic coating on the outer surface of each of the different types of catheters, the catheters were immersed in the base coat composition for a period of 10 seconds and then withdrawn at a rate of 0.7 cm/sec using a Harland PCX coating machine containing UV lamps. The base coat composition was then cured and dried under UV lamps for 45 seconds to form a base coat layer covering the outer surface of the catheter. The catheters were then immersed in the top coat composition for 10 seconds and withdrawn at a rate of 0.5 cm/sec. The top coat composition was then UV cured and dried under UV lamps for 10 minutes to form the top coat layer, resulting in the formation of a hydrophilic coating on the catheter.

The coated catheters of each catheter type were divided into two groups—non-sterilized catheters and sterilized catheters.

The non-sterilized catheters immersed in water for 30 seconds and then the initial and abraded Cops were measured. The sterilized catheters were "dry sterilized" in that they were individually packaged and sealed in dry foil pouches (i.e., no water or wetting fluid added to the package), and then gamma sterilized in the package at 30-35 kGy. The dry sterilized catheters were removed from their packages and immersed in water for 30 seconds prior to measure the initial and abraded CoFs. The CoFs were measured in the same manner as described above in Example 1.

Example 11

Results

Table 9 show the initial and abraded CoFs for each of the different catheters having the hydrophilic coating thereon.

TABLE 9

|  | Non-Sterilized | | Sterilized | |
| --- | --- | --- | --- | --- |
| Catheter | CoF Initial Avg. | CoF Abraded Avg. | CoF Initial Avg. | CoF Abraded Avg. |
| TPE 83A | 0.020 | 0.020 | 0.039 | 0.048 |
| TPE 87A | 0.024 | 0.022 | 0.035 | 0.037 |
| TPE 90A | 0.054 | 0.021 | 0.025 | 0.028 |
| PVC 82A | 0.020 | 0.022 | 0.018 | 0.020 |

Example 12

Hydrophilic coatings were formed on the outer surfaces of catheters made of thermoplastic elastomers (TPE) and catheters made from PVC. The TPE catheters were supplied by Raumedic and the shore hardness of the catheters was one of 83 A, 87 A or 90 A. The PVC catheters had a shore hardness of 82 A. The hydrophilic coatings were formed from a base coat layer and a top coat layer. The base coat composition was prepared as indicated below and was applied to each of the catheters to form a base coat layer on the outer surface of the catheter. Additionally, the top coat composition included the same components and was prepared in the same manner as described above in Example 2. The top coat composition was applied over the base coat layer to form the hydrophilic coating on the catheter.

The formulation of the base coat composition included the following components:

| Base Coat | |
|---|---|
| Component | Amount (w/w) |
| Ethanol | 96.64% |
| PVP K90 Fluka | 0.32% |
| Irgacure 2959 (BASF) | 0.13% |
| PEG400DA (SR344, Sartomer, inhibitor removed) | 2.75% |
| Ethyl Cellulose | 0.16% |

The base coat composition was prepared by slowly adding PVP to ethanol while mixing until the PVP was dissolved. PEG400DA, Ethyl Cellulose and Irgacure 2959 were then added and allowed to fully dissolve while the solution was stirred.

To form the hydrophilic coating on the outer surface of each of the different types of catheters, the catheters were immersed in the base coat composition for a period of 10 seconds and then withdrawn at a rate of 0.7 cm/sec using a Harland PCX coating machine containing UV lamps. The base coat composition was then cured and dried under UV lamps for 45 seconds to form a base coat layer covering the outer surface of the catheter. The catheters were then immersed in the top coat composition for 10 seconds and withdrawn at a rate of 0.5 cm/sec. The top coat composition was then UV cured and dried under UV lamps for 10 minutes to form the top coat layer, resulting in the formation of a hydrophilic coating on the catheter.

The coated catheters of each catheter type were divided into two groups—non-sterilized catheters and sterilized catheters.

The non-sterilized catheters immersed in water for 30 seconds and then the initial and abraded CoFs were measured. The sterilized catheters were "dry sterilized" in that they were individually packaged and sealed in dry foil pouches (i.e., no water or wetting fluid added to the package), and then gamma sterilized in the package at 30-35 kGy. The dry sterilized catheters were removed from their packages and immersed in water for 30 seconds prior to measure the initial and abraded CoFs. The CoFs were measured in the same manner as described above in Example 1.

Example 12

Results

Table 10 shows the initial and abraded CoFs for each of the different catheters having the hydrophilic coating thereon.

TABLE 10

| | Non-Sterilized | | Sterilized | |
|---|---|---|---|---|
| Catheter | CoF Initial Avg. | CoF Abraded Avg. | CoF Initial Avg. | CoF Abraded Avg. |
| TPE 83A | 0.039 | 0.048 | 0.025 | 0.011 |
| TPE 87A | 0.035 | 0.037 | 0.033 | 0.044 |
| TPE 90A | 0.025 | 0.28 | 0.026 | 0.052 |
| PVC 82A | 0.018 | 0.20 | 0.018 | 0.021 |

Example 13

Hydrophilic coatings were formed on the outer surfaces of catheters made of thermoplastic elastomers having a shore hardness of 87 A and PVC catheters having a shore hardness of 82 A. The hydrophilic coatings were formed from a base coat layer and a top coat layer. The below listed base coat composition was prepared as indicated below and was applied to each of the catheters to form a base coat layer on the outer surface of the catheter. Additionally, the top coat composition included the same components and was prepared in the same manner as described above in Example 2. The top coat composition was applied over the base coat layer to form the hydrophilic coating on the catheter.

The formulation of the base coat composition included the following components:

| Base Coat | |
|---|---|
| Component | Amount (w/w) |
| Ethanol | 93.75% |
| PVP K90 Fluka | 3.72% |
| Irgacure 2959 (BASF) | 0.03% |
| PEG400DA (SR344, Sartomer, inhibitor removed) | 2.50% |

The base coat composition was prepared by slowly adding PVP to ethanol while mixing until the PVP was dissolved. PEG400DA and Irgacure 2959 were then added and allowed to fully dissolve while the solution was stirred.

To form the hydrophilic coating on the outer surface of each of the different types of catheters, the catheters were immersed in the base coat composition for a period of 10 seconds and then withdrawn at a rate of 0.7 cm/sec using a Harland PDX coating machine containing UV lamps. The base coat composition was then cured and dried under UV lamps for 45 seconds to form a base coat layer covering the outer surface of the catheter. The catheters were then immersed in the top coat composition for 10 seconds and withdrawn at a rate of 0.5 cm/sec. The top coat composition was then UV cured and dried under UV lamps for 10 minutes to form the top coat layer, resulting in the formation of a hydrophilic coating on the catheter.

The sterilized catheters were "dry sterilized" in that they were individually packaged and sealed in dry foil pouches (i.e., no water or wetting fluid added to the package), and then gamma sterilized in the package at 30-35 kGy. The dry sterilized catheters were removed from their packages and immersed in water for 30 seconds prior to measure the initial and abraded CoFs. The initial and abraded CoFs were measured in the same manner as described above in Example 1.

Example 13

Results

Table 11 show the initial and abraded CoFs for each of the different catheters having the hydrophilic coating thereon.

TABLE 11

| | Sterilized | |
| Catheter | CoF Initial Avg. | CoF Abraded Avg. |
| --- | --- | --- |
| TPE 87A | 0.02 | 0.02 |
| PVC 82A | 0.02 | 0.01 |

Example 14

Hydrophilic coatings were formed on the outer surfaces of catheters made of thermoplastic elastomers having a shore hardness of 87 A and PVC catheters having a shore hardness of 82 A. The hydrophilic coatings were formed from a base coat layer and a top coat layer. The below listed base coat composition was prepared as indicated below and was applied to each of the catheters to form a base coat layer on the outer surface of the catheter. Additionally, the top coat composition included the same components and was prepared in the same manner as described above in Example 2. The top coat composition was applied over the base coat layer to form the hydrophilic coating on the catheter.

The formulation of the base coat composition included the following components:

| Base Coat | |
| --- | --- |
| Component | Amount (w/w) |
| Ethanol | 95.81% |
| PVP K90 (Fluka) | 1.28% |
| Irgacure 2959 (BASF) | 0.03% |
| PEG400DA (SR344, Sartomer, inhibitor removed) | 2.56% |
| Ethyl Cellulose | 0.32% |

The base coat composition was prepared by slowly adding PVP to ethanol while mixing until the PVP was dissolved. PEG400DA, Ethyl Cellulose and Irgacure 2959 were then added and allowed to fully dissolve while the solution was stirred.

To form the hydrophilic coating on the outer surface of each of the different types of catheters, the catheters were immersed in the base coat composition for a period of 10 seconds and then withdrawn at a rate of 0.7 cm/sec using a Harland PCX coating machine containing UV lamps. The base coat composition was then cured and dried under UV lamps for 45 seconds to form a base coat layer covering the outer surface of the catheter. The catheters were then immersed in the top coat composition for 10 seconds and withdrawn at a rate of 0.5 cm/sec. The top coat composition was then UV cured and dried under UV lamps for 10 minutes to form the top coat layer, resulting in the formation of a hydrophilic coating on the catheter.

The sterilized catheters were "dry sterilized" in that they were individually packaged and sealed in dry foil pouches (i.e., no water or wetting fluid added to the package), and then gamma sterilized in the package at 30-35 kGy. The dry sterilized catheters were removed from their packages and immersed in water for 30 seconds prior to measure the initial and abraded CoFs. The initial and abraded CoFs were measured in the same manner as described above in Example 1.

Example 14

Results

Table 12 show the initial and abraded CoFs for each of the different catheters having the hydrophilic coating thereon.

TABLE 12

| | Sterilized | |
| Catheter | CoF Initial Avg. | CoF Abraded Avg. |
| --- | --- | --- |
| TPE 87A | 0.03 | 0.02 |
| PVC 82A | 0.02 | 0.01 |

Example 15

In the following examples, hydrophilic coating compositions according to the present disclosure were made and applied to PVC catheters having a size of CH14 and a shore hardness of 82 A to form hydrophilic coatings on the surface of the catheters.

A base coat composition was prepared from the following components (in dry wt %):

| PVP K90 (Ashland) | 1.3 m mw | 80 wt % |
| --- | --- | --- |
| PEG4000A (Sartomer, inhibitor removed) | | 20 wt % |
| Irgacure 2959 photoinitiator (BASF) | | 0.15 wt % |

The base coat formulation was prepared by slowly adding PVP to methanol (solvent) while mixing until the PVP was dissolved. PEG400DA and Irgacure 2959 were then added and allowed to fully dissolve under stirring. The above solid components were 2 wt % of the solution.

The base composition was applied by immersing the catheters in the composition solution. The catheters were immersed for a period of 10 seconds and then withdrawn at a rate of 0.7 cm/sec using a Harland PDX coating machine containing UV lamps. The base coat composition was then cured and dried under UV lamps for 45 seconds to form a base coat layer on the catheter.

A top coat composition, designated top coat composition A, was prepared from the following components (in dry wt %):

| PVP K90 (Ashland) | 1.3 m mw | 81.25 wt % |
| --- | --- | --- |
| Polyacrylic acid-co-acrylamide (PAAc )(Mn 520K, 80% acrylamide) | | 8.4 wt % |
| Glycerol | | 8.4 wt % |
| PEG400DA (Sartomer, inhibitor removed) | | 1.7 wt % |
| BHT-alcohol | | 0.22 wt % |
| Secondary antioxidant | | 0.2 wt % |
| Benzophenone | | 0.15 wt % |

The PAAc was dissolved in a small amount of water until fully hydrated using an overhead stirrer. The ethanol and water (solvent) was then added slowly under mixing. PVP was then added slowly and mixed until dissolved. The remaining components (glycerol, PEG400DA, BHT-alcohol, benzophenone) were then added and allowed to fully dissolved. The ethanol to water ratio was 80:20 and the above solids were 7 wt %-8 wt % of the solution.

A second top coat composition, designated top coat composition B, was prepared from the following components (in dry wt %):

| PVP K90 (Ashland) | 1.3 m mw | 88.9 wt % |
| --- | --- | --- |
| Glycerol | | 8.15 wt % |
| PEG4000A (Sartomer, inhibitor removed) | | 1.84 wt % |

| | |
|---|---|
| BHT-alcohol | 0.22 wt % |
| Benzophenone | 0.16 wt % |

PVP was added slowly to an ethanol/water blend of 80% by weight of ethanol and 20 wt % water and mixed until dissolved. The remaining ingredients (glycerol, PEG400DA, BHT-alcohol, benzophenone) were then added and allowed to fully dissolve under stirring. The coating solids were 7% by weight of the solution.

Catheters already coated with the base coat layer were then immersed into one of compositions of top coat A and top coat B using a Harland PDX coating machine. The coating process involved a 10 second immersion in the coating fluid followed by retraction from the fluid at a rate of 0.5 cm/sec. The coating was UV cured and dried under UV lamps for 10 minutes to form a hydrophilic coating on the catheter.

The CoFs of the catheter samples were measured after the catheters were force hydrated by being immersed in water for 30 seconds. The initial, abraded and ten minute dry-out time CoFs of each type of catheter were measured as described above in Example 1. The catheters were non-sterilized, "dry sterilized" or "wet sterilized." The "dry sterilized" catheters were individually packaged and sealed in dry foil pouches (i.e., no water or wetting fluid added to the package). The "dry sterilized" catheters were then gamma sterilized in the package at 30-35 kGy. The "wet sterilized" catheters were immersed and force hydrated in water for 60 seconds and then individually packaged and sealed in a foil pack containing 8 mL of water in a gas permeable, liquid impermeable water reservoir. Once the catheter was placed inside of the foil pack, the foil pack was sealed. The liquid water remained in the gas permeable reservoir, such that the liquid water did not come into contact with the coating. The liquid water produced water vapor that formed a humid atmosphere in the package. Packages of this type are currently used for vapor hydrating catheters, such as in Hollister's VaPro® vapor hydrated catheter products. The "wet sterilized" catheters were then gamma sterilized in the package at a dose of about 30-35 kGy.

Figure 13:
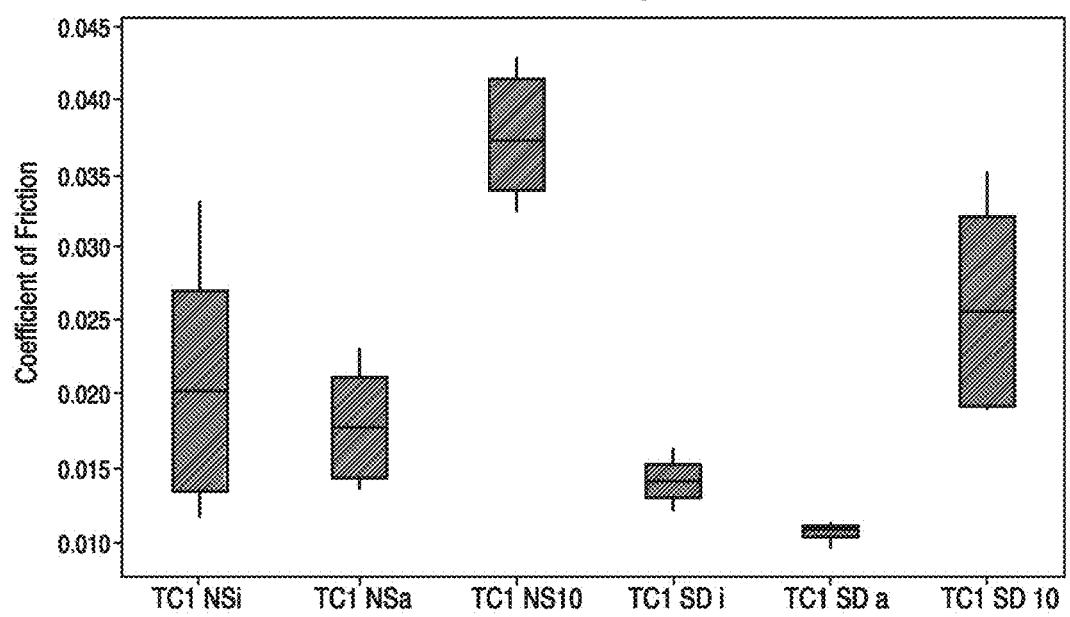
FIG. 13 is a graph representing the results of initial, abraded and ten-minute dry-out coefficient of friction measurements of non-sterilized and "dry sterilized" catheters coated with a base coat layer and top coat layer A of Example 15.

FIG. 13 shows the results of the CoF measurements for non-sterilized catheters having a coating formed from the base coat and top coat A after initial wetting (NSi), abrading (NSa) and 10 minute dry-out (NS10). FIG. 1 also shows the results of the CoF measures for "dry sterilized" catheters having a coating formed from the base coat and top coat A after initial wetting (SDi), abrading (SDa) and 10 minute dry-out (SD10).

Figure 14:
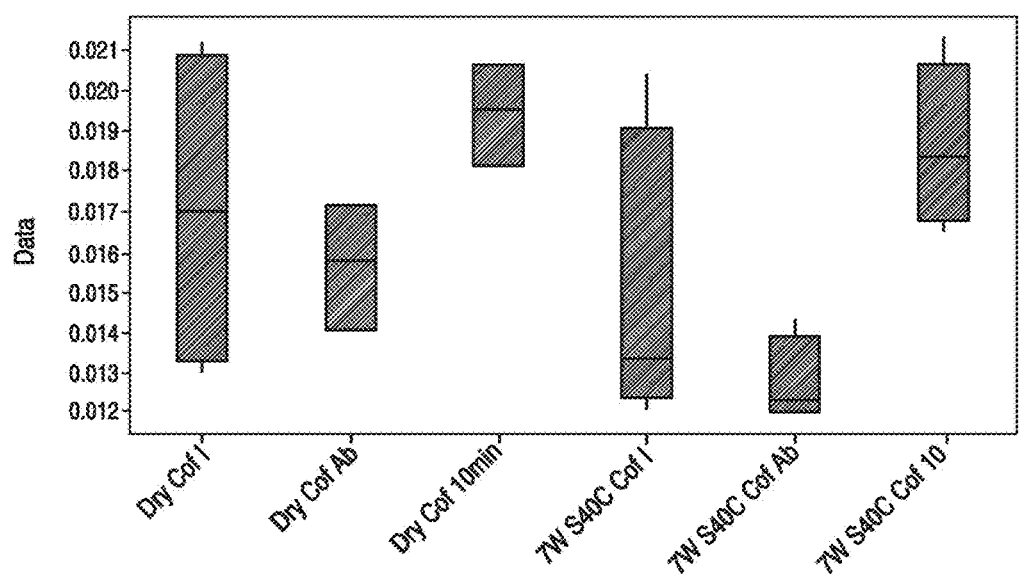
FIG. 14 is a graph representing the results of initial, abraded and ten-minute dry-out coefficient of friction measurements of "dry sterilized" catheters and "dry sterilized," accelerated aged catheters coated with a base coat layer and top coat layer A of Example 15.

FIG. 14 shows the results of the CoF measurements for "dry sterilized" catheters having a coating formed from the base coat and top coat A after initial wetting (Dry CoF I), abrading (Dry CoF Ab) and 10 minute dry-out (Dry CoF 10 min). FIG. 14 also shows the results of the initial (7W S400 CoF I), abraded (7W S400 CoF Ab), and 10 minute dry-out (7W S400 CoF 10) CoF measurements for "dry sterilized" catheters that underwent an accelerated aging process wherein the packaged catheters were aged for 7 weeks at 40° C. in a temperature controlled oven.

Figure 15:
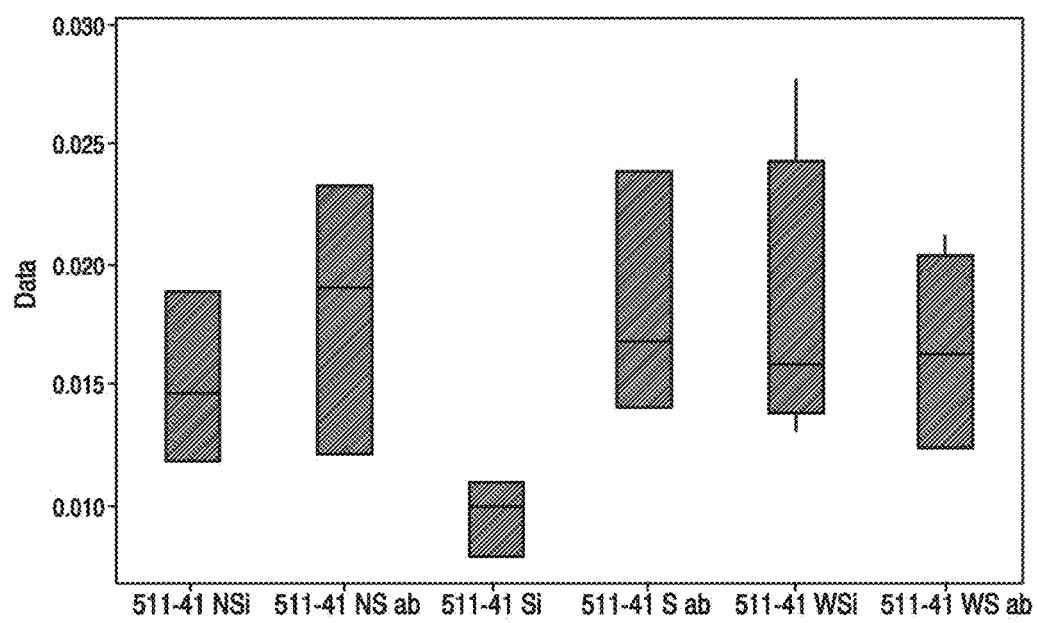
FIG. 15 is a graph representing the results of initial, abraded and ten-minute dry-out coefficient of friction measurements of non-sterilized and "dry sterilized" catheters coated with a base coat layer and top coat layer B Example 15.

FIG. 15 shows the results of the initial and abraded CoF measurements for non-sterilized, "dry sterilized" and "wet sterilized" catheters having a hydrophilic coating formed from the base coat and top coat B.

Aspects of the present subject matter described above may be beneficial alone or in combination with one or more other aspects. Without limiting the foregoing description, in accordance with a first aspect, a medical device including a hydrophilic coating disposed on a surface of the medical device, comprising: a base coat layer disposed on the surface of the medical device; and a top coat layer disposed on the base coat layer wherein the top coat layer is formed from a blend comprising a hydrophilic polymer and polyethylene glycol diacrylate having a number average molecular weight of less than about 1000.

Aspect 2. The medical device of aspect 1 wherein the hydrophilic polymer of the top coat layer comprises polyvinylpyrrolidone.

Aspect 3. The medical device of any one of the preceding aspects wherein the number average molecular weight of the polyethylene glycol diacrylate of the top coat layer is less than about 600.

Aspect 4. The medical device of any one of the preceding aspects wherein the polyethylene glycol diacrylate of the top coat layer has a number average molecular weight between about 200 and about 600.

Aspect 5. The medical device of any one of the preceding aspects wherein the top coat layer comprises about 80 wt % to about 95.5 wt % hydrophilic polymer and about 0.5 wt % to about 20 wt % polyethylene glycol diacrylate.

Aspect 6. The medical device of any one of the preceding aspects wherein the top coat layer comprises about 94 wt % to about 98 wt % hydrophilic polymer and about 2 wt % to about 6 wt % polyethylene glycol diacrylate.

Aspect 7, The medical device of any one of the proceeding aspects wherein the top coat layer comprises a polyethylene glycol diacrylate as a partially immiscible or an immiscible component.

Aspect 8. The medical any of the proceeding aspects wherein the polyethylene glycol diacrylate comprises a discrete, continuous or bi-continuous phase within the coating.

Aspect 9. The medical device of any one of the proceeding aspects wherein the polyethylene glycol diacrylate is phase separated from the hydrophilic polymer.

Aspect 10. The medical device of any one of aspects 7-9 wherein the top coat layer comprises a phase separated morphology comprising a continuous phase of polyvinylpyrrolidone and a discontinuous phase of polyethylene glycol diacrylate.

Aspect 11. The medical device of any one of the preceding aspects wherein the base coat layer comprises a diacrylate compound.

Aspect 12. The medical device of aspect 11 wherein the diacrylate compound of the base coat layer comprises polyethylene glycol diacrylate.

Aspect 13. The medical device of any one of aspects 11 and 12 wherein the diacrylate compound of the base coat layer has a number average molecular weight of less than about 1000.

Aspect 14. The medical device of any one of aspects 11-13 wherein the diacrylate compound of the base coat layer has a number average molecular weight of less than about 600.

Aspect 15. The medical device of any one of aspects 11-14 wherein the diacrylate compound of the base coat layer has a number average molecular weight between about 200 and about 600.

Aspect 16. The medical device of any one of aspects 11-15 wherein the base coat layer comprises a hydrophilic polymer.

Aspect 17. The medical device of aspect 16 wherein the hydrophilic polymer of the base coat layer comprises polyvinylpyrrolidone.

Aspect 18. The medical device of any one of the preceding aspects wherein the base coat layer comprises at least two immiscible or partially immiscible components.

Aspect 19. The medical device of any one aspects 16-18 wherein the polyethylene glycol diacrylate comprises a discrete, continuous or bi-continuous phase within the coating.

Aspect 20. The medical device of any one of the preceding aspects wherein the base coat layer comprises about 10 wt % to about 95 wt % hydrophilic polymer and about 5 wt % to about 90 wt % diacrylate compound.

Aspect 21. The medical device of any one of the preceding aspects wherein the medical device comprises a urinary catheter.

Aspect 22. The medical device of any one of the preceding aspects wherein the top coat layer further comprises a plasticizing agent.

Aspect 23. The medical device of aspect 22 wherein the plasticizing agent comprises glycerol.

Aspect 24. The medical device of any one of the preceding aspects wherein the top coat layer further comprises a curing agent and/or an antioxidant.

Aspect 25. A hydrophilic coating, comprising: an outer layer comprising a hydrophilic polymer and polyethylene glycol diacrylate having a number average molecular weight of less than about 1000.

Aspect 26. The hydrophilic coating of aspect 25 wherein the hydrophilic polymer of the outer layer comprises polyvinylpyrrolidone.

Aspect 27. The hydrophilic coating of any one of aspects 25 and 26 wherein the number average molecular weight of the polyethylene glycol diacrylate of the outer layer is less than about 600.

Aspect 28. The hydrophilic coating of any one of aspects 15-27 wherein the number average molecular weight of the polyethylene glycol diacrylate of the outer layer is between about 200 and about 600.

Aspect 29. The hydrophilic coating of any one of aspects 25-28 wherein the out layer comprises about 80 wt % to about 99.5 wt % hydrophilic polymer and about 0.5 wt % to about 20 wt % polyethylene glycol diacrylate.

Aspect 30. The hydrophilic coating of any one of aspects 25-29 wherein the outer layer comprises about 94 wt % to about 99.5 wt % hydrophilic polymer and about 2 wt % to about 6 wt % polyethylene glycol diacrylate.

Aspect 31. The hydrophilic coating of any one of aspects 25-30 wherein the top coat layer comprises a polyethylene glycol diacrylate as a partially immiscible or an immiscible component.

Aspect 32. The hydrophilic coating of any one of aspects 25-31 wherein the polyethylene glycol diacrylate comprises a discrete, continuous or bi-continuous phase within the coating.

Aspect 33. The hydrophilic coating of any one of aspects 25-32 wherein the top coat layer comprises a phase separated morphology comprising a continuous phase of polyvinylpyrrolidone and a discontinuous phase of polyethylene glycol diacrylate.

Aspect 34. The hydrophilic coating of any one of aspects 25-33 further including an inner layer.

Aspect 35. The hydrophilic coating of aspect 34 wherein the inner layer comprises a diacrylate compound.

Aspect 36. The hydrophilic coating of aspect 35 wherein the diacrylate compound of the inner layer comprises polyethylene glycol diacrylate.

Aspect 37. The hydrophilic coating of any one of aspects 35 and 36 wherein the diacrylate compound of the inner layer has a number average molecular weight of less than about 1000.

Aspect 38. The hydrophilic coating of any one of aspects 35-37 wherein the diacrylate compound of the inner layer has a number average molecular weight of less than about 600.

Aspect 39. The hydrophilic coating of any one of aspects 35-38 wherein the diacrylate compound of the inner layer has a number average molecular weight between about 200 and about 600.

Aspect 40. The hydrophilic coating of any one of aspects 34-39 wherein the inner layer comprises a hydrophilic polymer.

Aspect 41. The hydrophilic coating of aspect 40 wherein the hydrophilic polymer of the inner layer comprises polyvinylpyrrolidone.

Aspect 42. The hydrophilic coating of any one of aspects 34-41 wherein the inner layer comprises at least two immiscible or partially immiscible phases.

Aspect 43. The hydrophilic coating of any one aspect 34-42 wherein polyethylene glycol diacrylate comprises a discrete, continuous or bi-continuous phase within the coating.

Aspect 44. The hydrophilic coating of any one of aspects 40-43 wherein the inner layer comprises about 10 wt % to about 95 wt % hydrophilic polymer and about 5 wt % to about 90 wt % diacrylate compound.

Aspect 45. The hydrophilic coating of any one of aspects 25-44 wherein the hydrophilic coating comprises a urinary catheter.

Aspect 46. A method of forming a hydrophilic coating on a surface of a medical device, the method comprising: applying a base coat composition to the surface; curing the base coat composition to form a base coat layer; applying a top coat composition to the base coat layer, the top coat composition comprising a hydrophilic polymer and polyethylene diacrylate having a number average molecular weight of less than 1000; and curing the top coat composition to form a top coat layer.

Aspect 47. The method of aspect 45 wherein the polyethylene glycol diacrylate of the top coat layer has a number average molecular weight between about 200 and about 600.

Aspect 48. The method of any one of aspects 47 and 47 wherein the top coat composition further includes an alcohol.

Aspect 49. The method of aspect 48 wherein the alcohol comprises methanol, propanol, isopropyl alcohol or ethanol.

Aspect 50. The method of aspect 46-49 wherein the top coat composition comprises (a) about 89 wt % to about 97.5 wt % solvent; (b) about 2 wt % to about 10 wt % hydrophilic polymer; (c) about 0.1 wt % to about 0.6 wt % polyethylene glycol diacrylate; and (d) about 0.005 wt % to about 0.1 wt % curing agent.

Aspect 51. The method of aspect 50 wherein the top coat composition further comprises (e) about 2 wt % to about 12 wt % plasticizer; and (f) about 0.005 wt % to about 0.2 wt % antioxidant.

Aspect 52. The method of any one of aspects 50 and 51 wherein the solvent comprises a mixture of water and alcohol.

Aspect 53. The method of any one of aspects 46-52 wherein the drying and curing of the top coat composition results in the polyethylene glycol diacrylate forming a separate phase within the top coating layer.

Aspect 54. The method of any one of aspects 46-53 wherein the drying and curing the top coat composition results in the polyethylene glycol diacrylate being a discrete, continuous or bi-continuous phase within the top coat layer.

Aspect 55. The method of any one of aspect 46-54 wherein drying and curing the top coat composition results in the polyethylene glycol diacrylate phase separating from the hydrophilic polymer.

Aspect 56. The method of any one of aspects 46-55 wherein the base coat composition comprises a diacrylate compound.

Aspect 57. The method of aspect 56 wherein the diacrylate compound of the base coat layer comprises polyethylene glycol diacrylate.

Aspect 58. The method of any one of aspects 56 and 57 wherein the diacrylate compound of the base coat layer has a number average molecular weight between about 200 and about 600.

Aspect 59. The method of any one of aspects 46-48 wherein the base coat composition comprises a hydrophilic polymer.

Aspect 60. The method of aspect 59 wherein the hydrophilic polymer of the base coat composition comprises polyvinylpyrrolidone.

Aspect 61. The method of any one of aspects 59-60 wherein drying and curing of the base coat composition results in the base coat layer having at least two immiscible or partially immiscible components.

Aspect 62. The method of any one aspects 59-61 wherein wherein drying and curing the base coat composition results in the diacrylate compound being a discrete, continuous or bi-continuous phase within the coating.

Aspect 63. The method of any one of aspects 57-63 wherein the base coat composition comprises about 0.5 wt % to about 10 wt % hydrophilic polymer, about 0.1 wt % to about 5 wt % diacrylate compound, about 0.01 wt % to about 1 wt % curing agent, and about 90 wt % to 99.5 wt % solvent.

Aspect 64. The method of any one of aspects 45-63 wherein the medical device comprises a urinary catheter.

Aspect 65. A medical device including a hydrophilic coating disposed on a surface of the medical device, comprising: a base coat layer disposed on the surface of the medical device wherein the base coat layer is formed from a blend comprising a hydrophilic polymer and polyethylene glycol diacrylate having a number average molecular weight of less than about 1000; and a top coat layer disposed on the base coat layer.

Aspect 66. The medical device of any one of aspects 65 wherein the polyethylene glycol diacrylate compound of the base coat layer has a number average molecular weight of less than about 600.

Aspect 67. The medical device of any one of aspects 65 and 66 wherein the polyethylene glycol diacrylate compound of the base coat layer has a number average molecular weight between about 200 and about 600.

Aspect 68. The medical device of any one of aspects 65-67 wherein the hydrophilic polymer of the base coat layer comprises polyvinylpyrrolidone.

Aspect 69. The medical device of any one of aspects 65-67 wherein the base coat layer comprises a phase separated morphology.

Aspect 70. The medical device of any one of aspects 65-69 wherein the top coat layer comprises a hydrophilic polymer.

Aspect 71. The medical device of any one of aspect 65-70 wherein the top coat layer comprises a diacrylate compound.

Aspect 72. A medical device including a hydrophilic coating disposed on a surface of the medical device, comprising: a base coat layer disposed on the surface of the medical device wherein the base coat layer is formed from a blend comprising a cellulose based polymer and a hydrophilic polymer; and a top coat layer disposed on the base coat layer wherein the top coat layer comprises a hydrophilic polymer.

Aspect 73. The medical device of aspect 72 wherein the cellulose based polymer comprises one or more of methyl cellulose, ethyl cellulose, hydroxyl methylcellulose, hydroxypropyl cellulose, and hydroxypropyl methylcellulose.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A method of forming a hydrophilic coating on a surface of a medical device, the method comprising:
    applying a hydrophilic coating composition to the surface of the medical device, the hydrophilic coating composition comprising (i) polyethylene glycol diacrylate having a number average molecular weight of less than 1000 and (ii) a hydrophilic polymer comprising polyvinylpyrrolidone; and
    drying and/or curing the hydrophilic coating composition to form a hydrophilic coating wherein the polyethylene glycol diacrylate is a discrete, continuous or bi-continuous phase within the hydrophilic coating.

2. The method of claim 1 wherein the number average molecular weight of the polyethylene glycol diacrylate of the hydrophilic coating composition is between about 200 and about 600.

3. The method of claim 1 wherein the hydrophilic coating composition further includes an alcohol.

4. The method of claim 3 wherein the alcohol comprises methanol, propanol, isopropyl alcohol or ethanol.

5. The method of claim 1 wherein the hydrophilic coating composition comprises
    (a) about 89 wt % to about 97.5 wt % solvent;
    (b) about 2 wt % to about 10 wt % hydrophilic polymer;
    (c) about 0.1 wt % to about 0.6 wt % polyethylene glycol diacrylate; and
    (d) about 0.005 wt % to about 0.1 wt % curing agent.

6. The method of claim 5 wherein the hydrophilic coating composition further comprises
    (e) about 2 wt % to about 12 wt % plasticizer; and
    (f) about 0.005 wt % to about 0.2 wt % antioxidant.

7. The method of claim 5 wherein the solvent comprises a mixture of water and alcohol.

8. The method of claim 1 wherein the hydrophilic coating comprises a phase separated morphology comprising a continuous phase of polyvinylpyrrolidone and a discontinuous phase of polyethylene glycol diacrylate.

9. The method of claim 1 wherein the hydrophilic coating comprises about 94 wt % to about 98 wt % hydrophilic polymer and about 2 wt % to about 6 wt % polyethylene glycol diacrylate.

10. The method of claim 1 wherein the number average molecular weight of the polyethylene glycol diacrylate is less than about 600.

11. The method of claim 1 wherein the polyvinylpyrrolidone comprises a molecular weight of at least 500,000.

12. The method of claim 1 wherein the medical device comprises a urinary catheter.

13. A method of forming a hydrophilic coating on a surface of a medical device, the method comprising:
   applying a hydrophilic coating composition to the surface of the medical device, the hydrophilic coating composition comprising (i) a hydrophilic polymer comprising polyvinylpyrrolidone, and (ii) polyethylene glycol diacrylate having a number average molecular weight of less than 1000; and
   drying and/or curing the hydrophilic coating composition to form a hydrophilic layer wherein the polyethylene glycol diacrylate is phase separated from the polyvinylpyrrolidone within the hydrophilic coating.

14. The method of claim 13 wherein the number average molecular weight of the polyethylene glycol diacrylate of the hydrophilic coating composition is between about 200 and about 600.

15. The method of claim 13 wherein the hydrophilic coating composition further includes an alcohol.

16. The method of claim 15 wherein the alcohol comprises methanol, propanol, isopropyl alcohol or ethanol.

17. The method of claim 13 wherein the hydrophilic coating composition comprises
   (g) about 89 wt % to about 97.5 wt % solvent;
   (h) about 2 wt % to about 10 wt % hydrophilic polymer;
   (i) about 0.1 wt % to about 0.6 wt % polyethylene glycol diacrylate; and
   (j) about 0.005 wt % to about 0.1 wt % curing agent.

18. The method of claim 17 wherein the hydrophilic coating composition further comprises
   (k) about 2 wt % to about 12 wt % plasticizer; and
   (l) about 0.005 wt % to about 0.2 wt % antioxidant.

19. The method of claim 17 wherein the solvent comprises a mixture of water and alcohol.

20. The method of claim 13 wherein the hydrophilic coating comprises about 94 wt % to about 98 wt % hydrophilic polymer and about 2 wt % to about 6 wt % polyethylene glycol diacrylate.

21. The method of claim 13 wherein the number average molecular weight of the polyethylene glycol diacrylate is less than about 600.

22. The method of claim 13 wherein the polyvinylpyrrolidone comprises a molecular weight of at least 500,000.

23. The method of claim 13 wherein the medical device comprises a urinary catheter.

24. The method of claim 22 wherein the hydrophilic coating composition comprises
   (m) about 89 wt % to about 97.5 wt % solvent;
   (n) about 2 wt % to about 10 wt % hydrophilic polymer;
   (o) about 0.1 wt % to about 0.6 wt % polyethylene glycol diacrylate; and
   (p) about 0.005 wt % to about 0.1 wt % curing agent.

25. The method of claim 24 wherein the hydrophilic coating composition further comprises
   (q) about 2 wt % to about 12 wt % plasticizer; and
   (r) about 0.005 wt % to about 0.2 wt % antioxidant.

26. The method of claim 24 wherein the solvent comprises a mixture of water and alcohol.

27. A method of forming a hydrophilic coating on a surface of a medical device, the method comprising:
   applying a hydrophilic coating composition to the surface of the medical device, the hydrophilic coating composition comprising (i) a hydrophilic polymer comprising polyvinylpyrrolidone, and (ii) polyethylene glycol diacrylate having a number average molecular weight of less than 1000; and
   drying and/or curing the hydrophilic coating composition to form a hydrophilic layer wherein the polyethylene glycol diacrylate is a partially immiscible or an immiscible component.

28. The method of claim 27 wherein the number average molecular weight of the polyethylene glycol diacrylate of the hydrophilic coating composition is between about 200 and about 600.

29. The method of claim 27 wherein the hydrophilic coating composition further includes an alcohol.

30. The method of claim 29 wherein the alcohol comprises methanol, propanol, isopropyl alcohol or ethanol.

31. The method of claim 27 wherein the hydrophilic coating comprises about 94 wt % to about 98 wt % hydrophilic polymer and about 2 wt % to about 6 wt % polyethylene glycol diacrylate.

32. The method of claim 27 wherein the number average molecular weight of the polyethylene glycol diacrylate is less than about 600.

33. The method of claim 27 wherein the polyvinylpyrrolidone comprises a high molecular weight of at least 500,000.

34. The method of claim 27 wherein the medical device comprises a urinary catheter.

* * * * *